(12) United States Patent
Kim et al.

(10) Patent No.: US 10,808,952 B2
(45) Date of Patent: Oct. 20, 2020

(54) HUMIDIFIER AND HOME APPLIANCE

(71) Applicant: Samsung Electronics Co., Ltd., Suwon-si, Gyeonggi-do (KR)

(72) Inventors: Mun Sub Kim, Suwon-si (KR); Hyeong Joon Seo, Suwon-si (KR); Hoon Yeong Koh, Suwon-si (KR); Ju Hwan Kim, Suwon-si (KR); Jin Yong Mo, Anyang-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 16/557,829

(22) Filed: Aug. 30, 2019

(65) Prior Publication Data

US 2019/0383503 A1    Dec. 19, 2019

Related U.S. Application Data

(63) Continuation of application No. 15/081,658, filed on Mar. 25, 2016, now Pat. No. 10,436,466.

(30) Foreign Application Priority Data

Apr. 16, 2015   (KR) ........................ 10-2015-0053883

(51) Int. Cl.
*F24F 6/02*   (2006.01)
*F24F 13/24*  (2006.01)
(Continued)

(52) U.S. Cl.
CPC ................. *F24F 6/02* (2013.01); *F24F 6/00* (2013.01); *F24F 6/16* (2013.01); *F24F 11/74* (2018.01);
(Continued)

(58) Field of Classification Search
CPC ........ F24F 6/02; F24F 6/00; F24F 6/16; F24F 11/74; F24F 13/24; F24F 2006/008
See application file for complete search history.

(56) References Cited

U.S. PATENT DOCUMENTS 4,489,744 A * 12/1984 Merrill .................... F16K 15/04
                                                        137/202
4,500,480 A *  2/1985 Cambio, Jr. ......... A61M 16/164
                                                        128/200.11
(Continued)

FOREIGN PATENT DOCUMENTS

CN       103104014 A     5/2013
EP         2810921 A1   12/2014
(Continued)

OTHER PUBLICATIONS

Communication from a foreign patent office in a counterpart foreign application, European Patent Office, "Communication pursuant to Article 94(3) EPC," Application No. EP 16159876.8, dated Jul. 24, 2018, 4 pages.

(Continued)

*Primary Examiner* — Stephen Hobson

(57) ABSTRACT

Disclosed is a humidifier and home appliance having a structure with an air inflow path formed in a water tank separately from a water supply inlet and configured to prevent noise due to air bubbles during water supply to a water reservoir from the water tank, and a structure configured to block the air inflow path in order to prevent water from flowing into the air inflow path during replenishment of water to the water tank.

16 Claims, 27 Drawing Sheets

(51) Int. Cl.
*F24F 6/00* (2006.01)
*F24F 6/16* (2006.01)
*F24F 11/74* (2018.01)

(52) U.S. Cl.
CPC ........ *F24F 13/24* (2013.01); *F24F 2006/008* (2013.01)

(56) References Cited

U.S. PATENT DOCUMENTS

| | | | | |
|---|---|---|---|---|
| 4,765,327 A | * | 8/1988 | Shim | A61M 16/167 128/204.13 |
| 5,431,290 A | * | 7/1995 | Vinciguerra | A61J 9/04 137/845 |
| 5,547,615 A | * | 8/1996 | Jan e | F24F 6/04 261/24 |
| 6,248,155 B1 | * | 6/2001 | Seaman | F24F 6/043 95/211 |
| 6,997,183 B2 | * | 2/2006 | Koch | A61M 16/161 128/203.16 |
| 7,228,859 B2 | * | 6/2007 | Loescher | A61M 16/16 128/203.12 |
| 7,722,016 B2 | * | 5/2010 | Bradley | A61M 16/167 261/70 |
| 10,168,064 B1 | * | 1/2019 | Zhang | B05B 17/0607 |
| 2003/0016952 A1 | * | 1/2003 | Elphee | F24F 6/18 392/324 |
| 2004/0050386 A1 | * | 3/2004 | Levine | A61M 16/167 128/203.16 |
| 2006/0151624 A1 | * | 7/2006 | Grundler | A61M 13/003 237/67 |
| 2008/0093750 A1 | * | 4/2008 | Wang | F24F 6/00 261/66 |
| 2012/0012186 A1 | * | 1/2012 | Tantra | A61M 16/167 137/1 |
| 2012/0164935 A1 | * | 6/2012 | Ha | F24F 6/06 454/337 |
| 2013/0111657 A1 | | 5/2013 | Song | |
| 2013/0174843 A1 | * | 7/2013 | Smith | A61M 16/16 128/203.26 |
| 2014/0083524 A1 | * | 3/2014 | Huang | F16K 31/20 137/409 |
| 2014/0264963 A1 | * | 9/2014 | Barker | F24F 13/00 261/37 |
| 2017/0349456 A1 | * | 12/2017 | Ohdou | C02F 1/001 |

FOREIGN PATENT DOCUMENTS

| | | |
|---|---|---|
| JP | 2003240282 A | 8/2003 |
| JP | 3110210 U | 6/2005 |
| JP | 2008095988 A | 4/2008 |
| JP | 2010196933 A | 9/2010 |
| JP | 2013002797 A | 1/2013 |
| KR | 10-1996-0001651 A | 1/1996 |
| KR | 10-2008-0014165 A | 2/2008 |

OTHER PUBLICATIONS

European Patent Office, "Communication pursuant to Article 94(3) EPC," Application No. EP 16 159 876.8, dated Aug. 30, 2017, 4 pages.
Extended European Search Report dated Aug. 25, 2016 in connection with European Patent Application No. 16159876.8, 8 pages.
International Search Report dated Jun. 16, 2016 in connection with International Application No. PCT/KR2016/001733, 3 pages.
Office Action dated Jul. 3, 2019 in connection with Chinese Patent Application No. 201680035070.8, 17 pages.

\* cited by examiner

HUMIDIFIER AND HOME APPLIANCE

CROSS-REFERENCE TO RELATED APPLICATIONS

This application is a continuation of application Ser. No. 15/081,658, filed Mar. 25, 2016, which claims priority to Korean Patent Application No. 10-2015-0053883, filed Apr. 16, 2015, the entire disclosures of which are incorporated hereby incorporated by reference.

BACKGROUND

1. Field

The present disclosure relates to a humidifier and home appliance having a structure to prevent noise from being produced from a water tank during replenishment of water to a water reservoir.

2. Description of Related Art

Humidifiers are generally used to keep indoor humidity at an optimum level and prevent many respiratory problems.

The humidifier sprays water stored in the water reservoir in the form of droplets, or evaporates the water.

The humidifier is replenished with water from a water tank when the water level of the water reservoir drops below a certain level, and this makes unusual noise due to air bubbles going into the water tank.

SUMMARY

To address the above-discussed deficiencies, it is a primary object to provide, for use in a humidifier and home appliance including a structure with an air inflow path in a water tank of the humidifier, separate from a water supply inlet to prevent unusual noise due to air bubbles during water supply to a water reservoir from the water tank.

The present disclosure also provides a humidifier and home appliance including a structure configured to block an air inflow path to prevent water from flowing into the air inflow path during replenishment of water to a water tank of the humidifier.

In accordance with an aspect of the present disclosure, a home appliance is provided. The home appliance include a water tank including an air inflow device; and a water reservoir configured to contain water flowing in from the water tank, wherein the air inflow device comprises an air inflow path and an open/close unit configured to open or close the air inflow path.

The home appliance may further include a humidifying element configured to perform humidification with supplied water contained in the water reservoir.

The open/close unit may include a float configured to move according to a water level of the water reservoir; and an open/close member configured to open or close the air inflow path according to a height of the float.

The open/close member may open the air inflow path if the float falls, and close the air inflow path if the float rises.

The air inflow path may include an air inflow pipe opened or closed by the open/close unit; and an air tube connected to the air inflow pipe.

The open/close unit may include an airtight member configured to airtightly close the air inflow path.

The air inflow device may include a check valve configured to prevent water from flowing into the air inflow path from the water tank during replenishment of water to the water tank.

The check valve may include a recess configured to receive buoyant force.

In accordance with another aspect of the present disclosure, a humidifier is provided. The humidifier includes a water tank comprising a body and a cap; a water reservoir configured to contain water flowing in from the water tank; and a humidifying element configured to perform humidification with supplied water contained in the water reservoir, wherein the cap of the water tank is equipped with a water supply inlet configured to supply water to the water reservoir, and wherein the body of the water tank is equipped with an air inflow path and an open/close unit configured to open or close the air inflow path.

The open/close unit may include a float moving according to a water level of the water reservoir; and an open/close member configured to open or close the air inflow path according to a height of the float, wherein the air inflow path may include an air inflow pipe opened or closed by the open/close member; and an air tube connected to the air inflow pipe.

The open/close member may include an airtight member configured to airtightly close an air flow inlet of the air inflow pipe.

The air flow inlet of the air inflow pipe may be located farther away from the water reservoir than from the water supply inlet, wherein the air flow inlet is exposed to air if a water level of the water reservoir decreases, and the open/close member is configured to open the air flow inlet as the float falls, and wherein the float rises again and enables the open/close member to close the air flow inlet again, if water of the water tank flows into the water reservoir through the water supply inlet.

In accordance with another aspect of the present disclosure, a humidifier is provided. The humidifier includes a water tank comprising a body and a cap; a water reservoir configured to contain water flowing in from the water tank; and a humidifying element configured to receive supplied water from the water reservoir and perform humidification with the supplied water, wherein the cap of the water tank may include a water supply inlet configured to supply water to the water reservoir; an air inflow pipe configured to force air to flow into the water tank; an air tube configured to enable the air flowing into the air inflow pipe to be moved to a side opposite to the water supply inlet; and an open/close unit configured to open or close the air inflow pipe.

The air tube may have one end connected to the air inflow pipe, and the other end comprising a check valve configured to prevent water from flowing into the air tube.

An air flow inlet of the air inflow pipe may be located farther away from the water reservoir than from the water supply inlet, The open/close unit may include a float configured to move according to a water level of the water reservoir; and an open/close member connected to the float for opening or closing an air flow inlet of the air inflow pipe according to a height of the float.

The open/close member may have one end hinged with the float, and the other end having an airtight member configured to airtightly close the air flow inlet of the air inflow pipe, and the open/close member may be hinged with the cap such that both ends moves like a seesaw.

The float and the open/close member may be integrally formed, an air tight member may be arranged on the other end of the open/close member configured to airtightly close the air inflow pipe, and the open/close member may be hinged with the cap such that both ends moves like a seesaw.

The open/close unit may include a float configured to move according to a water level of the water reservoir, open the air inflow pipe if the float falls, and close the air inflow pipe if the float rises.

The float may have an airtight member configured to airtightly close an air flow inlet of the air inflow pipe.

The cap may have an anti-separation structure configured to prevent accidental separation of the float.

Other aspects, advantages, and salient features of the disclosure will become apparent to those skilled in the art from the following detailed description, which, taken in conjunction with the annexed drawings, discloses exemplary embodiments of the disclosure.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts.

Throughout the drawings, like reference numerals will be understood to refer to like parts, components, and structures.

DETAILED DESCRIPTION

FIGS. 1 through 24, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged device. There may be various types of humidifiers, such as heated humidifiers, ultrasonic humidifiers, complex humidifiers having a combination of heated and ultrasonic humidification functions, and evaporative humidifiers naturally evaporating water without use of ultrasounds or heater.

For convenience of explanation, embodiments of an evaporative humidifier will be described. However, the present disclosure is not limited thereto, and it is noted that any of the heated, ultrasound, and complex humidifiers may be used in some other embodiments. Moreover, it is noted that the present disclosure will also be applied in other devices requiring water supply.

Structure and operation of a humidifier in accordance with embodiments of the present disclosure will now be described with reference to accompanying drawings. As used herein, the singular forms "a", "an" and "the" are intended to include the plural forms as well, unless the context clearly indicates otherwise. For the sake of clarity, the elements of the drawings are drawn with exaggerated forms and sizes.

Figure 1:
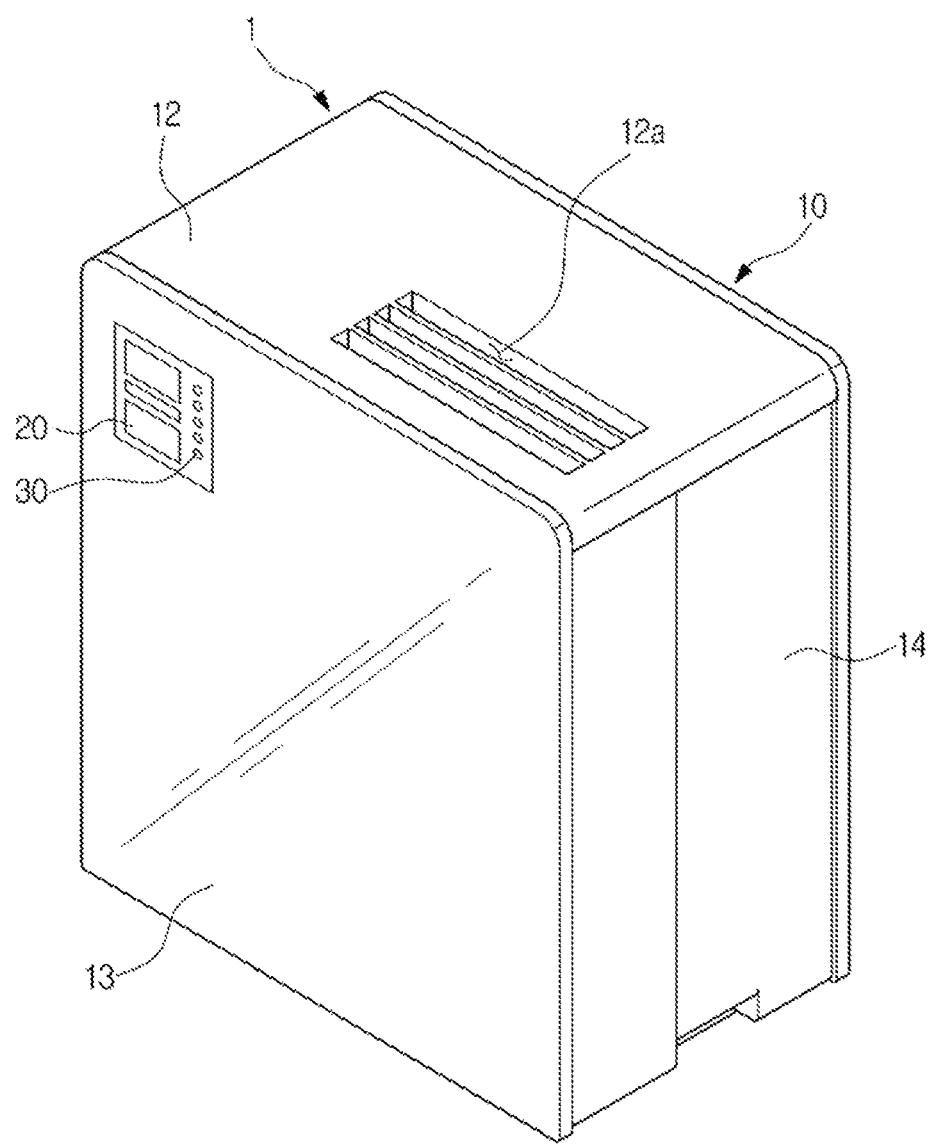
FIG. 1 illustrates a humidifier according to various embodiments of the present disclosure.
Figure 2:
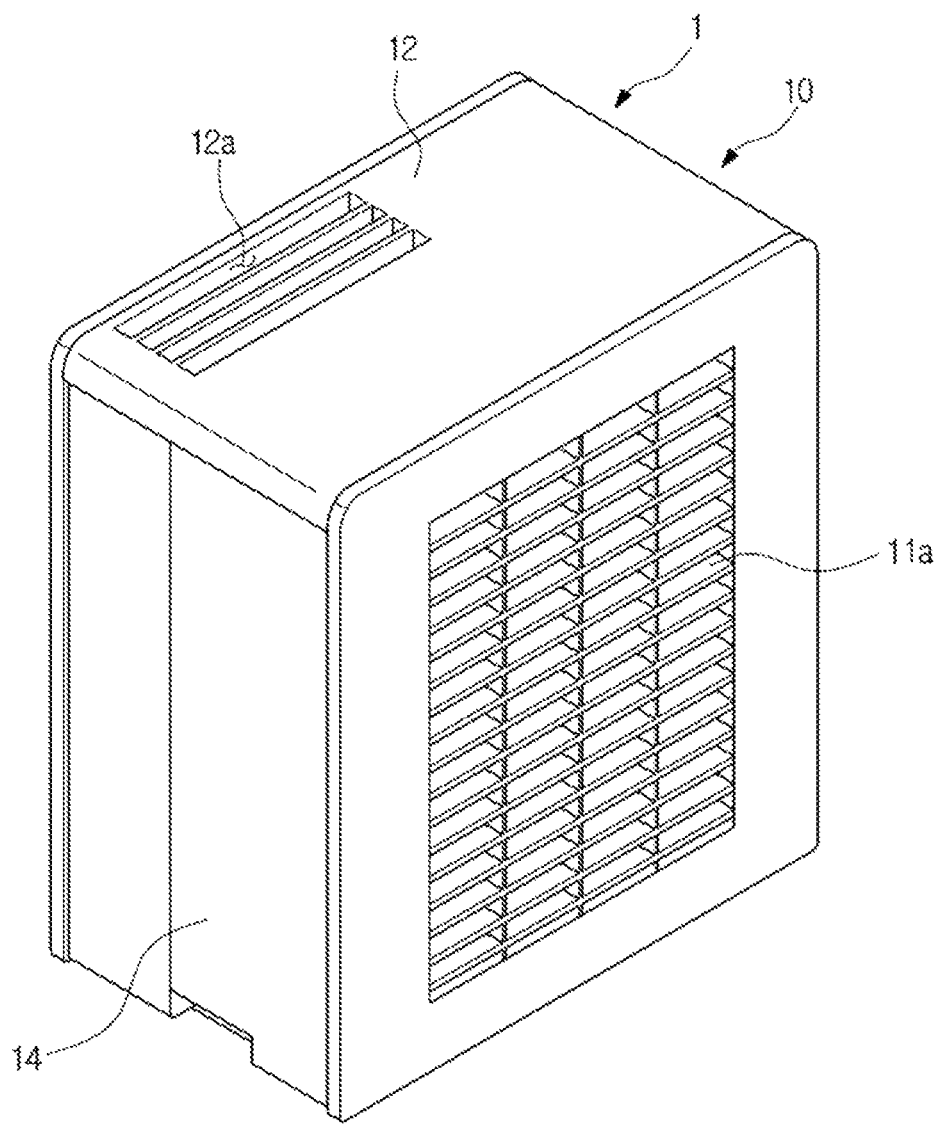
FIG. 2 illustrates the humidifier of FIG. 1 according to various embodiments of the present disclosure.
Figure 3:
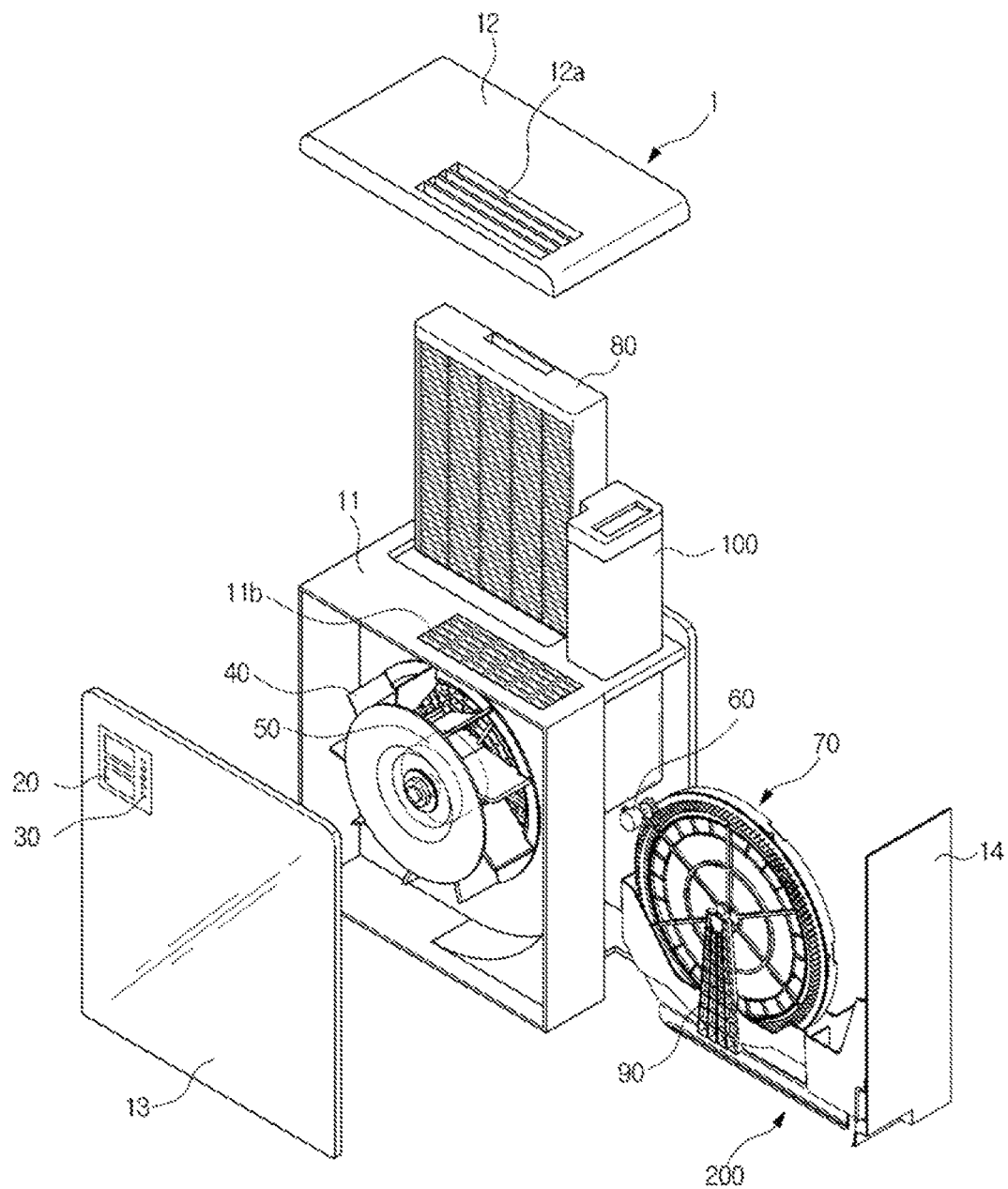
FIG. 3 illustrates the humidifier of FIG. 1 according to various embodiments of the present disclosure.

FIG. 1 is a front perspective view of a humidifier, according to an embodiment of the present disclosure, FIG. 2 is a rear perspective view of the humidifier of FIG. 1, and FIG. 3 is a front exploded view of the humidifier of FIG. 1.

Referring to FIGS. 1 to 3, a humidifier 1 in accordance with an embodiment may include a main frame 10 that constitutes an exterior, a blower fan 40 placed inside the main frame 10 for forcedly circulating air, a water reservoir 200 placed inside the main frame 10 for storing water, and a humidifying element 70 rotatably placed inside the main frame 10 for evaporating water supplied from the water reservoir 200.

The main frame 10 may include a main housing 11, a front cover 13 coupled onto a front opening of the main housing 11, a side cover coupled onto a side opening of the main housing 11, and a top cover 12 coupled onto the top of the main housing 11.

An inlet 11a is formed on the rear side of the main housing 11 to enable dry indoor air to flow to the inside of main frame 10, and an outlet 11b is formed on the top of the main housing 11 to discharge wet air from humidification inside the main frame 10 back into the room. A grill unit 12a is formed on the top cover 12 to correspond to the outlet 11b.

Accordingly, the dry indoor air may flow to the inside of the main frame 10 through the inlet 11a on the rear side of the main frame 10, be humidified in the main frame 10, and be discharged upward through the outlet 11b of the main frame 10.

Such forced circulation of the air may be done by the blower fan 40. Specifically, the blower fan 40 may be a concentric fan, which may be rotated by a first motor 50 to produce an air current to move the air in the back of the main frame 10 upward of the main frame 10.

A display unit 20 for displaying various information regarding the humidifier 1, and an input unit 30 for activating various functions of the humidifier 1 may be mounted on the front cover 13.

The humidifying element 70 may be rotatably supported by a supporting frame 90. The humidifying element 70 may be rotated by turning force delivered from a second motor 60.

The supporting frame 90 is combined with the water reservoir 200. The humidifying element 70 may be separated from the supporting frame 90. Specifically, after removal of the side cover 14, the water reservoir 200 and the humidifying element 70 may be mounted in or separated out of the main frame 10 in the lateral direction.

The humidifier 1 may include a filter unit 80 for purifying air flowing into the main frame 10, and a water tank 100 for supplying water to the water reservoir 200.

The filter unit 80 may include a dust collection filter, deodorization filter, etc. That is, the humidifier 1 may also perform air purification. After removal of the top cover 12, the filter unit 80 and the water tank 100 may be mounted in or separated out of the main frame 10 in the longitudinal direction.

The water tank 100 may serve to store water necessary for humidification and supply a proper amount of the water to the water reservoir 200. The water tank 100 may be equipped in the humidifier like a cassette unit.

Figure 4:
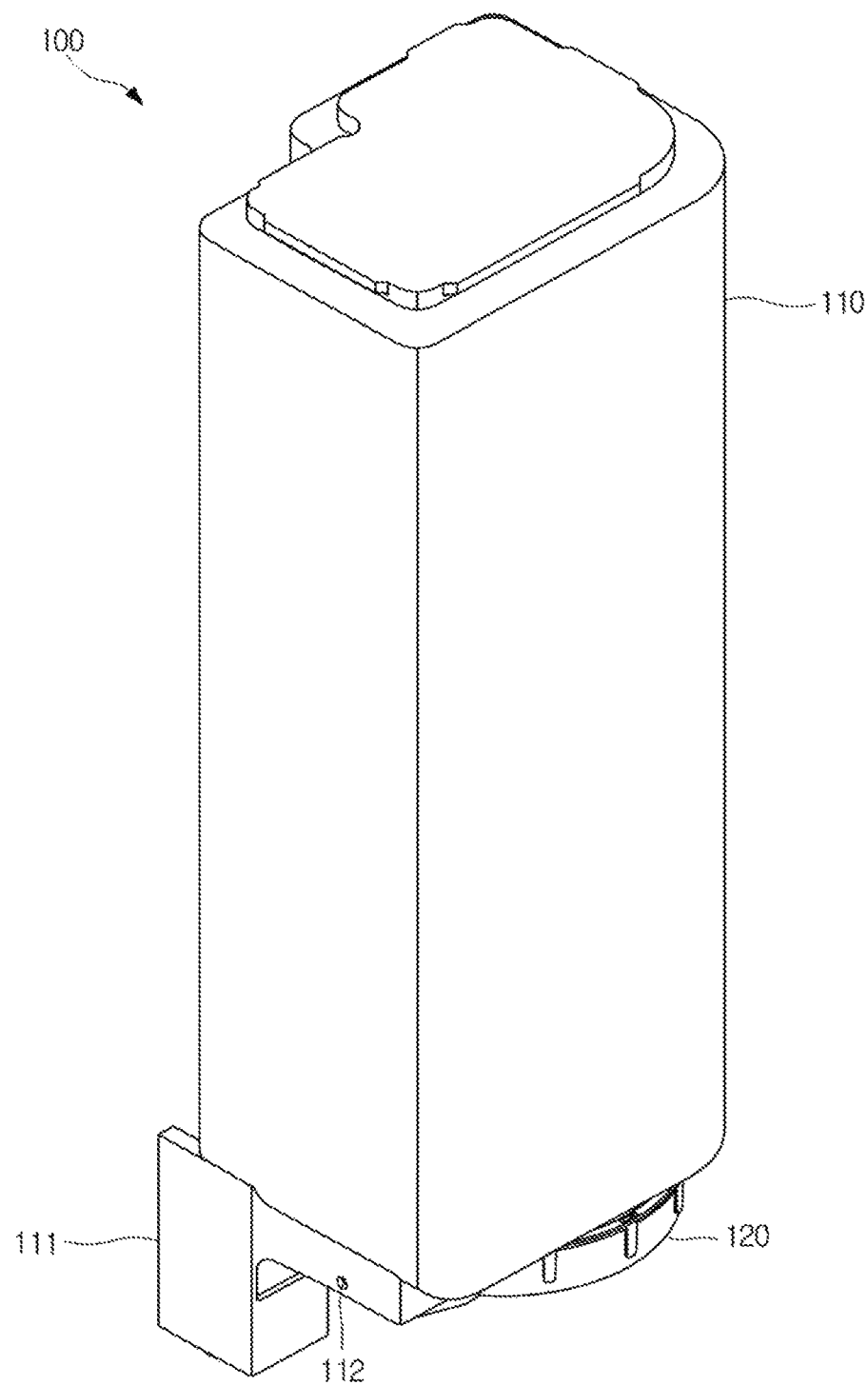
FIG. 4 illustrates a water tank according to various embodiments of the present disclosure.
Figure 5:
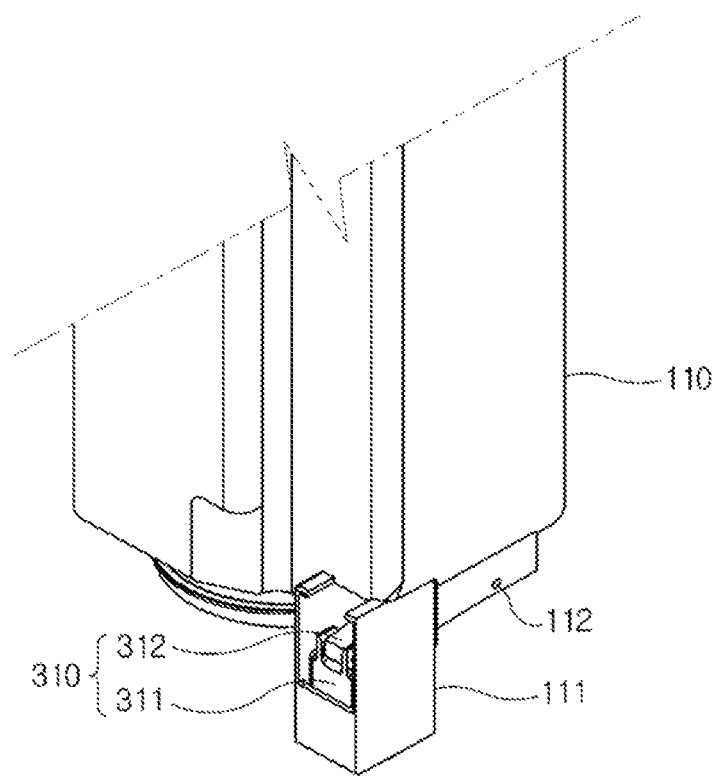
FIG. 5 illustrates a bottom part of the water tank of FIG. 4, from which a cap is pulled apart according to various embodiments of the present disclosure.
Figure 6:
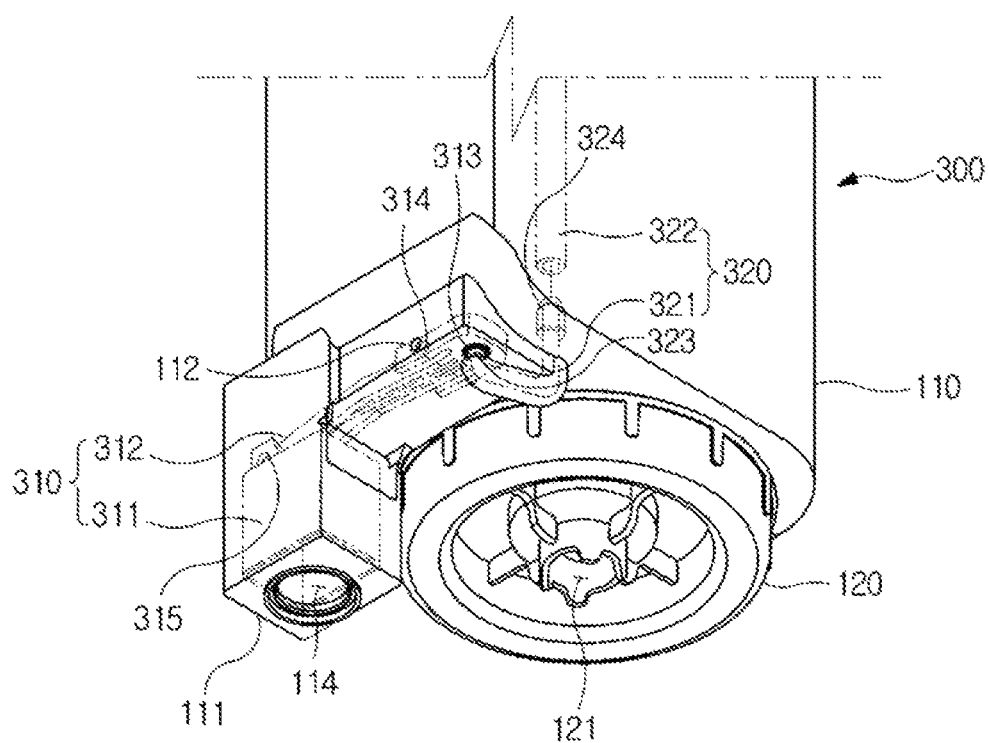
FIG. 6 illustrates an air inflow device equipped in the water tank of FIG. 4 according to various embodiments of the present disclosure.
Figure 7:
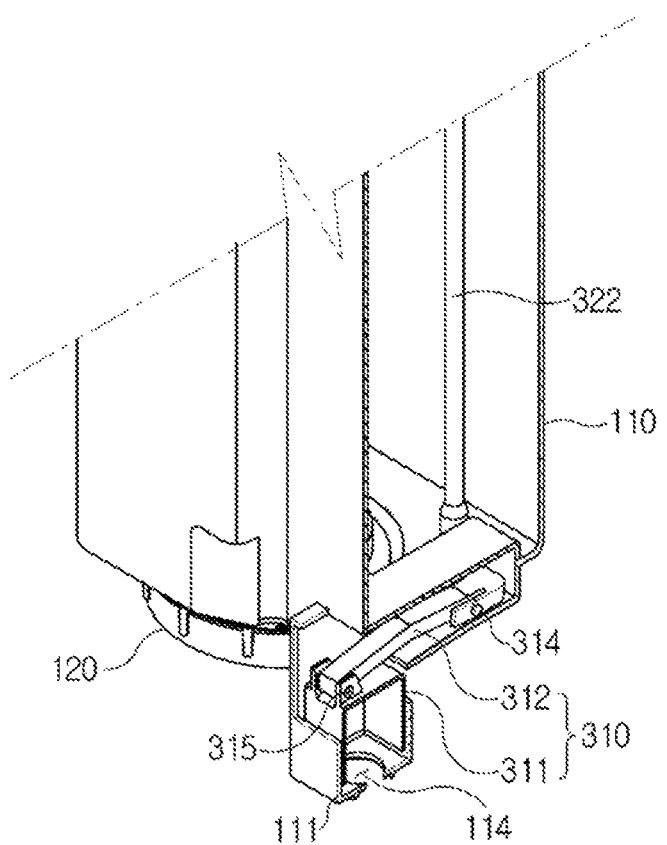
FIG. 7 illustrates the water tank of FIG. 4 viewed by cutting an air inflow device according to various embodiments of the present disclosure.

A structure of the water tank will now be described in connection with FIGS. 4 to 7. FIG. 4 is a front perspective view of a water tank, according to an embodiment of the present disclosure, and FIG. 5 is an exploded view of a bottom part of the water tank of FIG. 4, from which a cap is pulled apart. FIG. 6 is a perspective view of an air inflow device equipped in the water tank of FIG. 4, and FIG. 7 is a cross-sectional view of the water tank of FIG. 4 viewed by cutting the air inflow device.

Referring to FIGS. 4 and 5, the water tank 100 may include a body 110, and a cap 120 mounted on the bottom of the body 110. The cap 120 may include a cap airtight member 122 for airtightly close the water tank 100 while the cap 120 is combined with the body 110. The cap airtight member 122 may be formed of an elastic material, such as rubber.

The cap 120 may also include a water supply inlet 121 for supplying water stored in the water tank 100 to the water reservoir 200. In the water supply inlet 121, a water supply valve 123 may be arranged to open the water supply inlet 121 while the water tank 100 is mounted in the humidifier 1, and to close the water supply inlet 121 while the water tank 100 is separated from the humidifier 1. The water supply valve 123 may be installed in the water supply inlet 121 by means of an elastic member 124. At this time, when the water tank 100 is mounted in the water reservoir 200 of the humidifier 1, the water supply valve 123 may be pushed up by a projection (not shown) formed in the water reservoir 200, to open the water supply inlet 121.

When a water level 201 of the water reservoir 200 decreases due to evaporation of the water by the humidifying element 70, air flows into the water tank 100 and pushes the water out of the water tank 100, achieving water supply. When outside air flows in through the water supply inlet 121, unusual noise is produced while air bubbles are passing through the water stored in the water tank 100.

Referring to FIGS. 4 to 7, an air inflow device 300 may be equipped on the bottom side of the body 110 of the water tank 100, in accordance with an embodiment of the present disclosure. The air inflow device 300 may introduce an air inflow path 320, which is separate from the water supply unit 121, to force the air to flow in without passing through the water stored in the water tank 100.

The air inflow device 300 may also include an open/close unit 310 to open or close the air inflow path 320. The open/close unit 310 may be contained in a housing 111 arranged on the bottom side of the body 110 of the water tank 100.

The open/close unit 310 may include a float 311 that is moved by buoyant force according to the water level 201 of the water reservoir 200, and an open/close member 312 for opening or closing the air inflow path 320 according to a height of the float 311. The open/close member 312 and the float 311 may be hinged through a hinge connector 315. The hinge connector 315 may combine the open/close member 312 and the float 311 by combining a hinge projection formed on the open/close member 312 and a hinge projection receptor hole formed on the float 311.

In the housing 111, an opening 114 to allow water to flow in from the water reservoir 200 for the float 311 to be moved according to changes of the water level 201 of the water reservoir 200 may be formed below the float 311. The float 311 may be formed in the form of a recess with the bottom face opened to float in water, or in the form of a box with the inside empty and closed.

The open/close member 312 has one end connected to the float 311 through the hinge connector 315, and the other end to be able to open/close the air inflow path 320. The ends of the open/close member 312 moves like a seesaw, in order for the open/close member 312 to open the air inflow path 320 if the float 311 falls, and to close the air inflow path 320 if the float 311 rises.

The open/close member 312 may have a hinge projection 314 formed between both ends of the open/close member 312 to enable the ends to move like a seesaw. The hinge projection 314 of the open/close member 312 may be combined into a hinge projection receptor hole 112 formed in the housing 111.

The air inflow path 320 may include an air inflow pipe 321 formed in the body 110 of the water tank 100, and an air tube 322 having one end connected to the air inflow pipe 321 to move the air upward of the inside of the water tank 100. An air flow inlet 323, which is opened or closed by the open/close unit 310, is formed on one end of the air inflow pipe 321, and a connector projection 324 to be connected to the air tube 322 is formed on the other end of the air inflow pipe 321. Specifically, the air flow inlet 323 is formed inside the housing 111 to be opened/closed by the open/close member 312, and the air tube connector projection 324 is arranged inside the body 110.

The air tube 322 is formed of a rubber or plastic material to couple with the connector projection 324 by fitting the connector projection 324 into the air tube 322. The air tube 322 may be formed of a non-flexible material to be able to deliver air from an end where the cap 120 of the water tank 100 is placed to the other end, or may be formed of a flexible material with sufficient length.

The open/close unit 310 may include an airtight member 313 formed to airtightly close the air flow path 320, specifically, the air flow inlet 323 of the air inflow pipe 321. The airtight member 313 may be formed of a material such as rubber.

Figure 8:
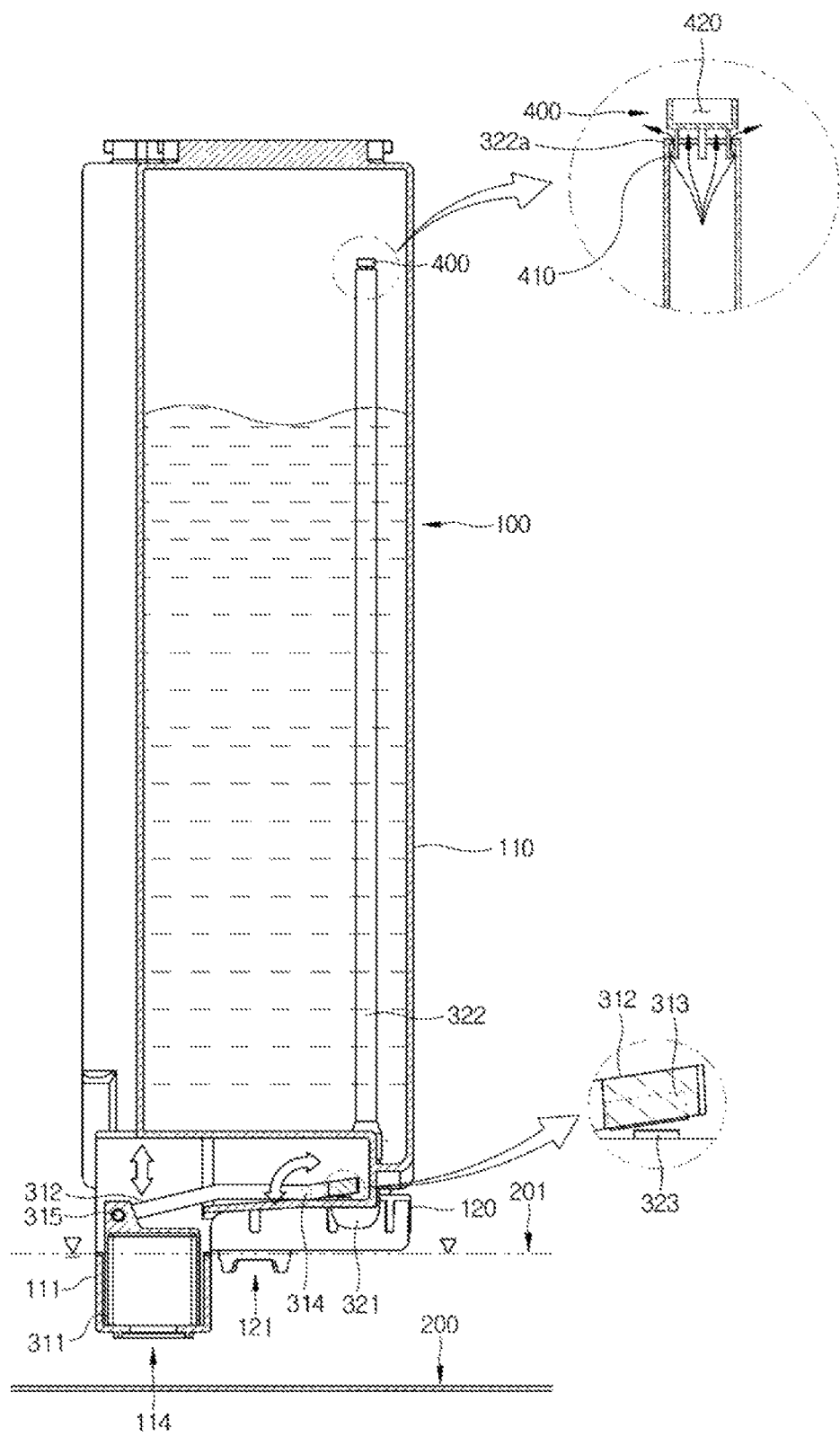
FIG. 8 illustrates the water tank of FIG. 4 for illustrating operations of the air inflow device and a check valve according to various embodiments of the present disclosure.
Figure 9:
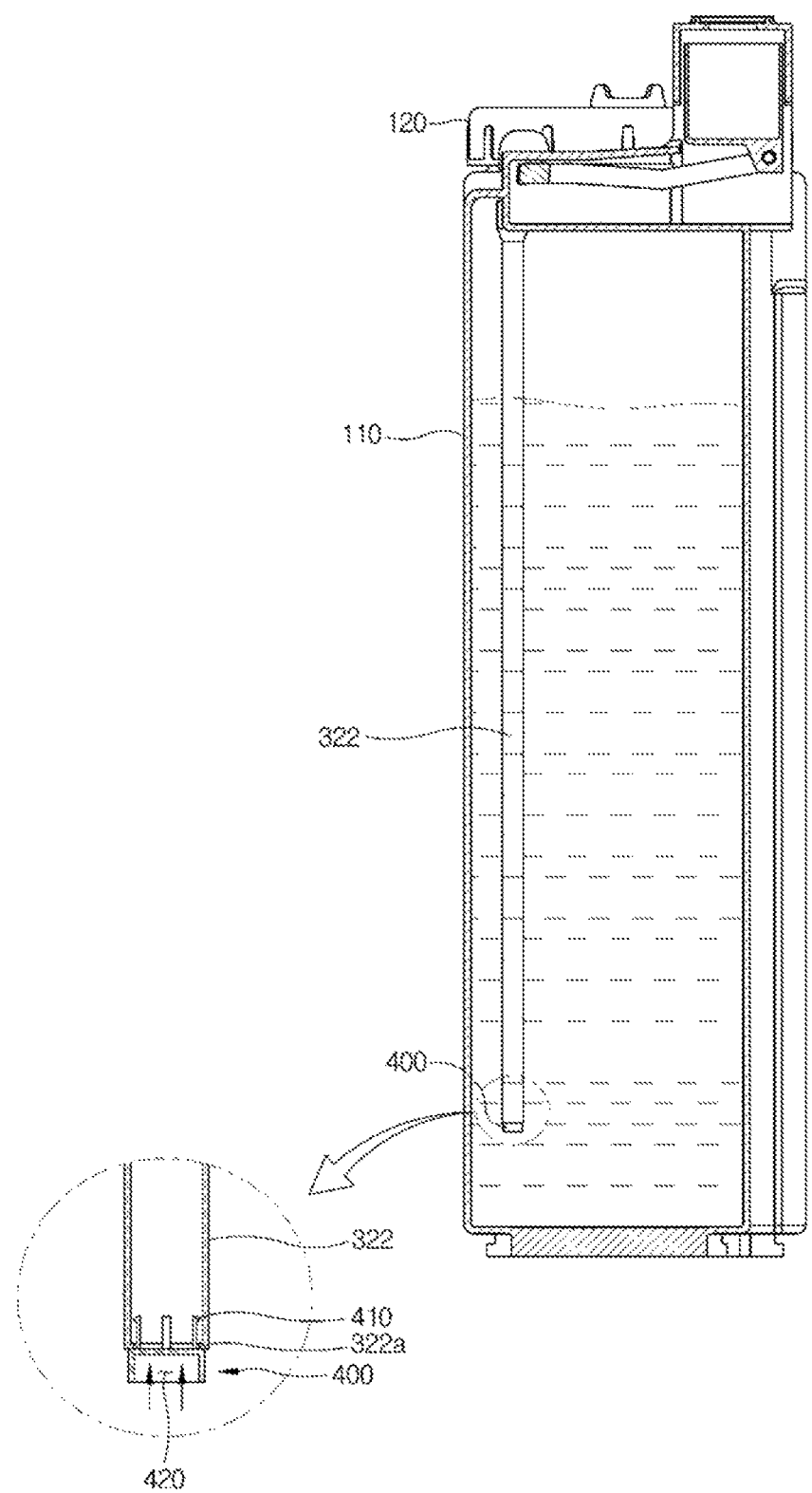
FIG. 9 illustrates the water tank of FIG. 4 for illustrating a check valve closed when the water tank is turned upside down according to various embodiments of the present disclosure.
Figure 10:
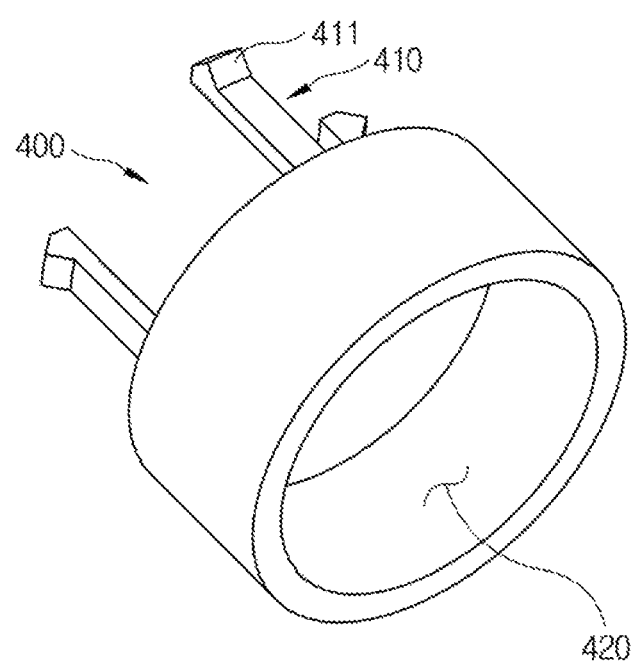
FIG. 10 illustrates a check valve that may close an air tube during replenishment of water to a water tank according to various embodiments of the present disclosure.
Figure 11:
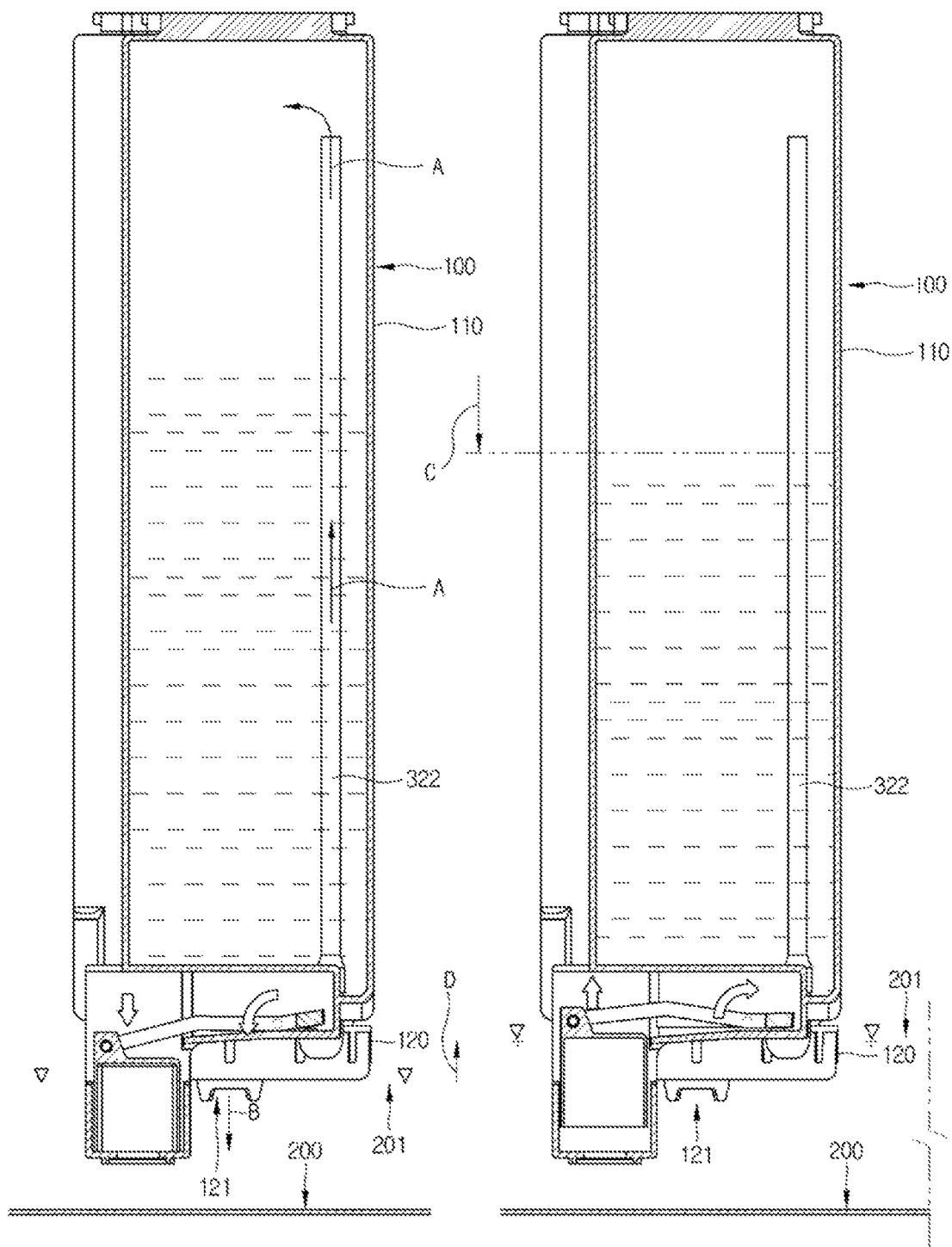
FIG. 11 illustrates a process of water supply from the water tank of FIG. 4 to a water reservoir according to various embodiments of the present disclosure.

An air inflow mechanism of the air inflow device 300, and a check valve 400 arranged on an end of the air tube 322 will now be described in connection with FIGS. 8 to 11. FIG. 8 is a cross-sectional view of the water tank of FIG. 4 for illustrating operations of the air inflow device and a check valve, and FIG. 9 is a cross-sectional view of the water tank of FIG. 4 for illustrating a check valve closed when the water tank is turned upside down. FIG. 10 is a perspective view of a check valve that may close the air tube during replenishment of water to the water tank. FIG. 11 illustrates a process of water supply from the water tank of FIG. 4 to the water reservoir.

Referring to FIGS. 8 to 10, as described above, an end of the air tube 322 may be coupled with the connector projection 324 of the air inflow tube 321 inside the body 110 of the water tank 100. On the other end of the air tube 322 not coupled with the connector projection 324, the check valve 400 may be arranged to prevent water contained in the water tank 100 from flowing into the air tube 322.

For example, in a case that the user turns the water tank 100 upside down with the cap 120 facing up, if the check valve 400 is not installed on the air tube 322, water may flow into the air tube 322, and the water flowing into the air tube 322 may be discharged through the air flow inlet 323 when the water tank 100 is turned upside down again to have the cap 120 face down.

The check valve 400 may include install members 410 to help the check valve 400 to be installed on the air tube 322. A hook 411 may be formed on the end of the install member 410 extending from the body of the check valve 400 to prevent it from being accidentally separated from the air tube 322. A hook receiver 322a may be formed on the end of the air tube 322 where the check valve 400 is mounted to catch the hook 411.

The check valve 400 may include a recess 420 formed to close the air tube 322 by buoyant force of the water contained in the water tank 100 while the water tank is turned upside down with the cap 120 facing up.

Referring to FIGS. 8 to 11, the float 311 of the open/close unit 310 may be moved up and down according to a height of the surface 201 of water of the water reservoir 200. As the float moves up and down, the end of the open/close member 312 coupled with the float 311 through the hinge connector 315 may also be moved up and down. The hinge projection 314 placed between the one end and the other end of the open/close member 312 may be mounted into the hinge projection receptor hole 112 of the housing 111.

As one end of the open/close member 312 is moved up and down by the hinge connection between the open/close member 312 and the housing 111, the other end of the open/close member 312 may also be moved up and down accordingly. This rotation movement (seesaw movement) of the open/close member 312 may enable the other end of the open/close member 312 to open or close the air flow inlet 323 of the air inflow pipe 321.

The closing member 313 may be arranged on the other end of the open/close member 312, i.e., the end to open or close the air flow inlet 323 to airtightly close the air flow inlet 323.

While the water tank 100 is mounted in the water reservoir 200, the air flow inlet 323 is arranged at a location farther away from the water reservoir 200 than from the water supply inlet 121 of the water tank 121. In other words, while the water tank 100 is mounted in the water reservoir 200, the air flow inlet 323 is arranged at a location higher than the water supply inlet 121 of the water tank 121.

Because the highest water level 201 of the water reservoir 200 is below the air flow inlet 323, the water of the water reservoir 200 may not flow into the air flow inlet 323. Alternatively, even if the highest water level 201 of the water reservoir 200 is above the air flow inlet 323, the water of the water reservoir 200 may not flow into the air flow inlet 323 because the open/close member 312 airtightly closes the air flow inlet 323.

As the water contained in the water reservoir 200 is used by the humidifying element 70 for humidification, the water level 201 of the water reservoir 200 falls. As the water level 201 of the water reservoir 201 falls, the float 311 may fall. As the float 311 falls, the open/close member 312 turns around the hinge projection 314 to open the air flow inlet 323.

Even if the highest water level 201 of the water reservoir is above the air flow inlet 323, the water of the water reservoir 200 may not flow into the air inflow pipe 321 even when the air flow inlet 323 is opened by the open/close member 312 because the air flow inlet 323 is first exposed to air when the water level 201 falls.

When the open/close member 312 opens the air flow inlet 323, outside air flows into the air inflow pipe 321, and the air flowing in (A) may be moved upward of the inside of the water tank 100 along the air tube 322. Due to the air inflow (A), the water stored in the water tank 100 may be supplied (B) to the water reservoir 200 through the water supply inlet 121.

As the water level of the water stored in the water tank 100 falls (C) due to the water supply (B), the water level 201 of the water reservoir 200 rises (D) again. As the water level 201 of the water reservoir 200 rises, the float 311 rises, causing the open/close member 312 to turn again around the hinge projection 314 to close the air flow inlet 323. When the air flow inlet 323 is closed by the open/close member 312, a vacuum is created in the water tank 100, and the water supply (B) may be stopped by pressure equalization.

By repeating the water supply process, the water tank 100 of the humidifier 1 in accordance with an embodiment of the present disclosure may maintain the water level 201 of the water reservoir 200 to a constant level while fundamentally preventing noise from being produced by air bubbles flowing into the water tank 100.

Another embodiment in which an air inflow device of a water tank is installed on the cap of the water tank in accordance with the present disclosure will now be described in connection with FIGS. 12 to 17.

Figure 12:
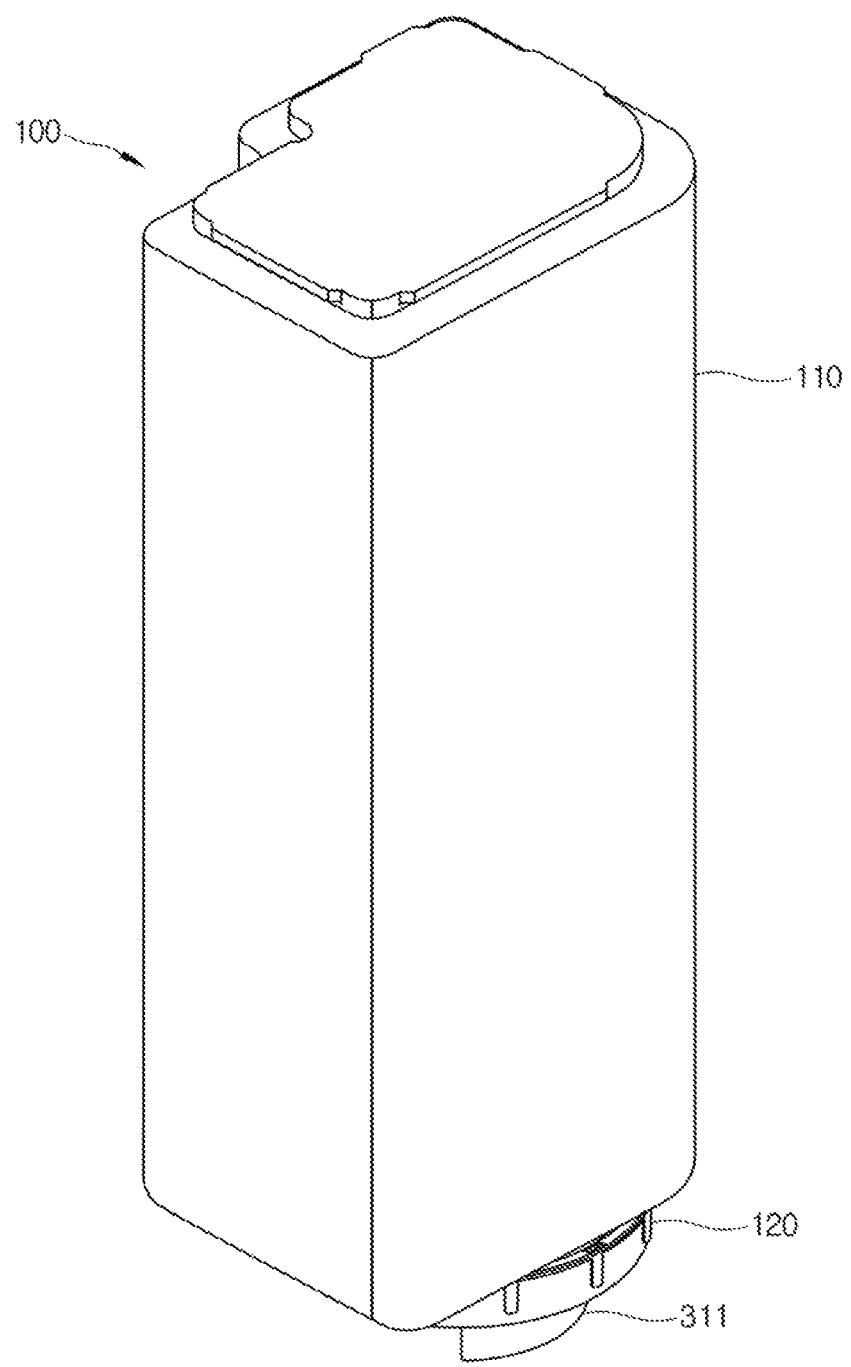
FIG. 12 illustrates a water tank according to various embodiments of the present disclosure.
Figure 13:
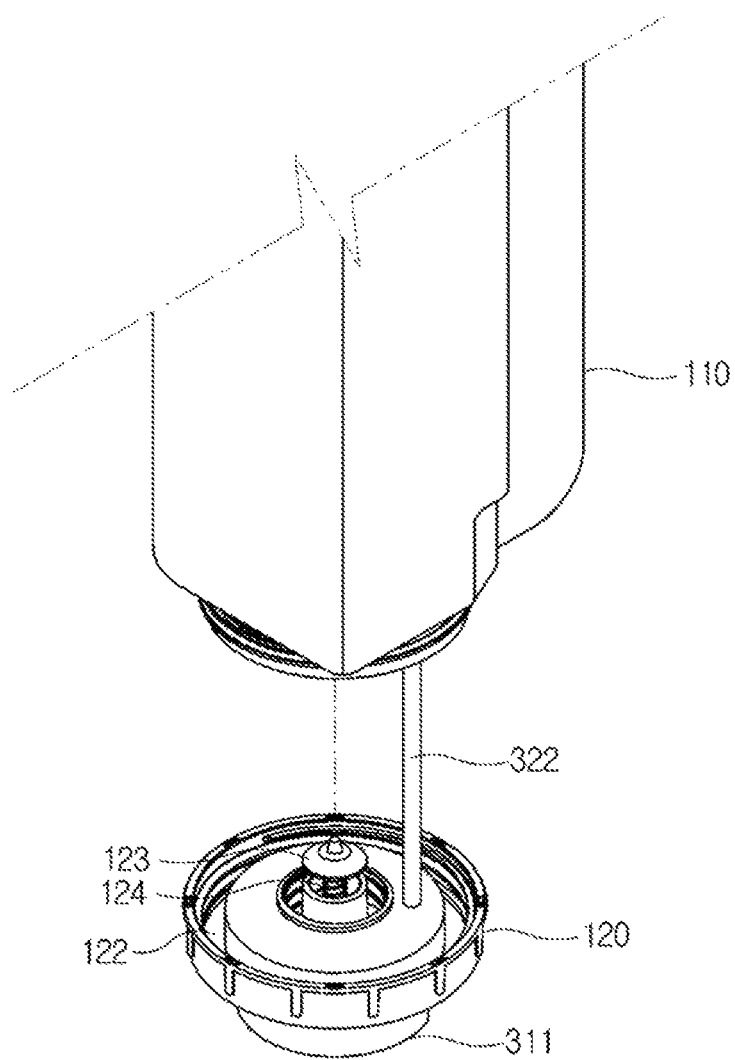
FIG. 13 illustrates a bottom part of the water tank of FIG. 12, from which a cap is pulled apart according to various embodiments of the present disclosure.
Figure 14:
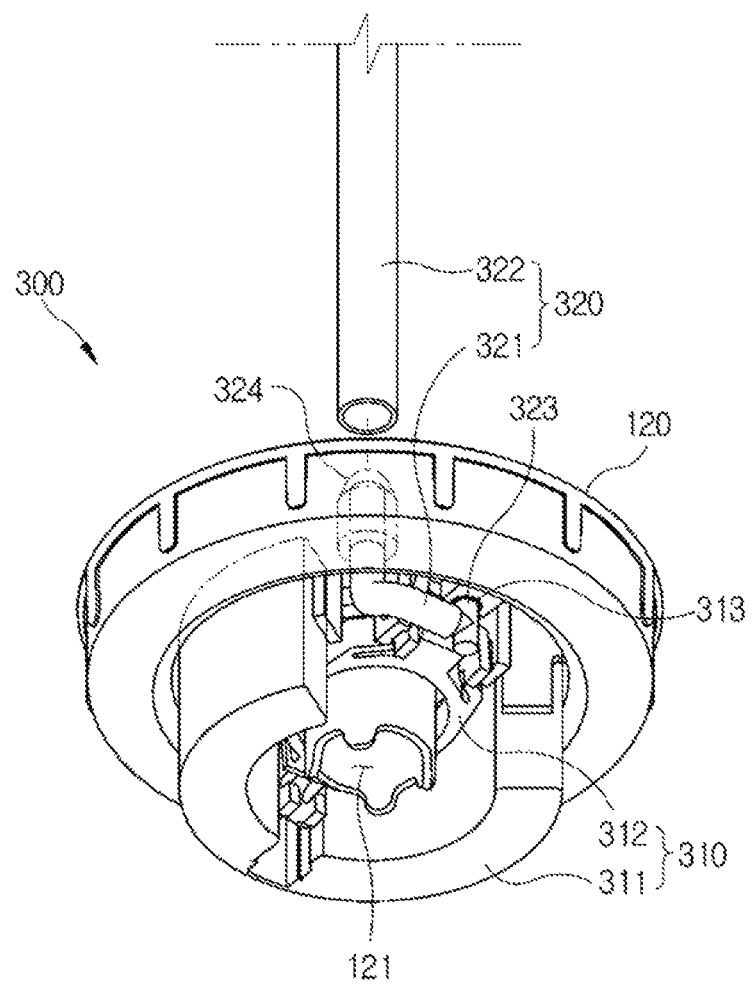
FIG. 14 illustrates a cap of the water tank of FIG. 12 according to various embodiments of the present disclosure.
Figure 15:
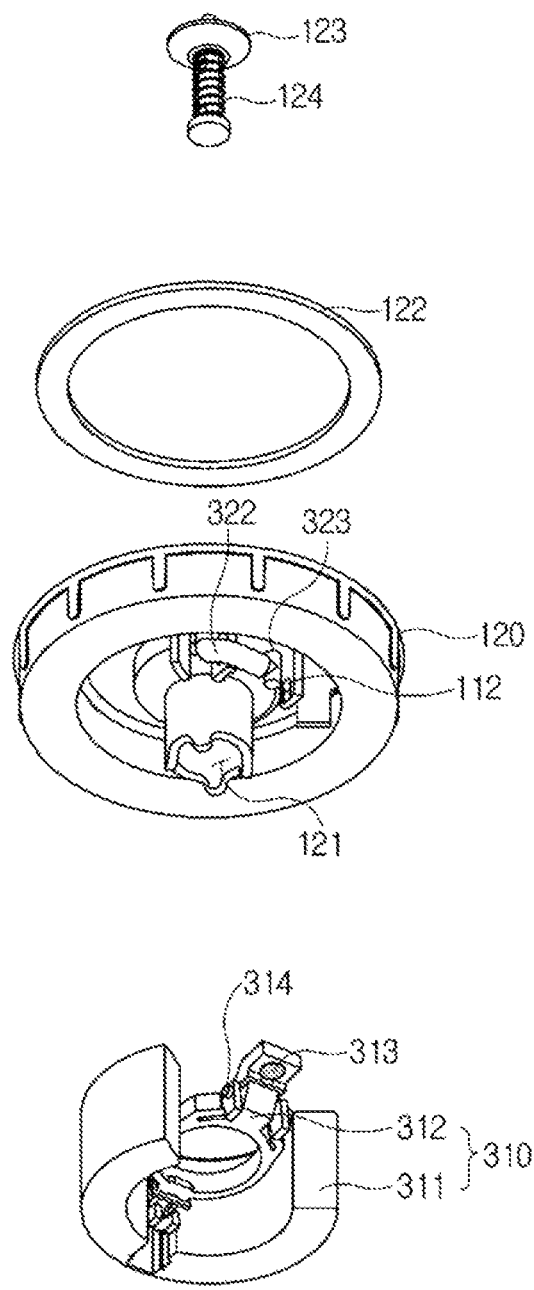
FIG. 15 illustrates a cap of the water tank of FIG. 12 according to various embodiments of the present disclosure.
Figure 16:
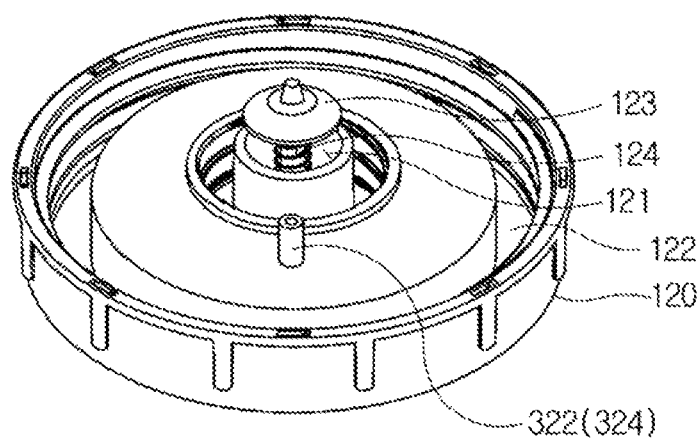
FIG. 16 illustrates an open/close unit of the water tank of FIG. 12 according to various embodiments of the present disclosure.
Figure 16:
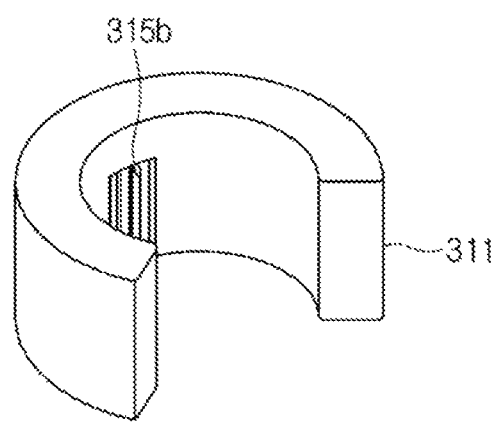
Figure 16:
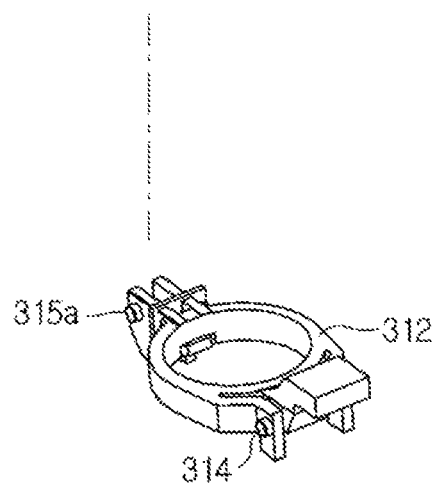
Figure 17A:
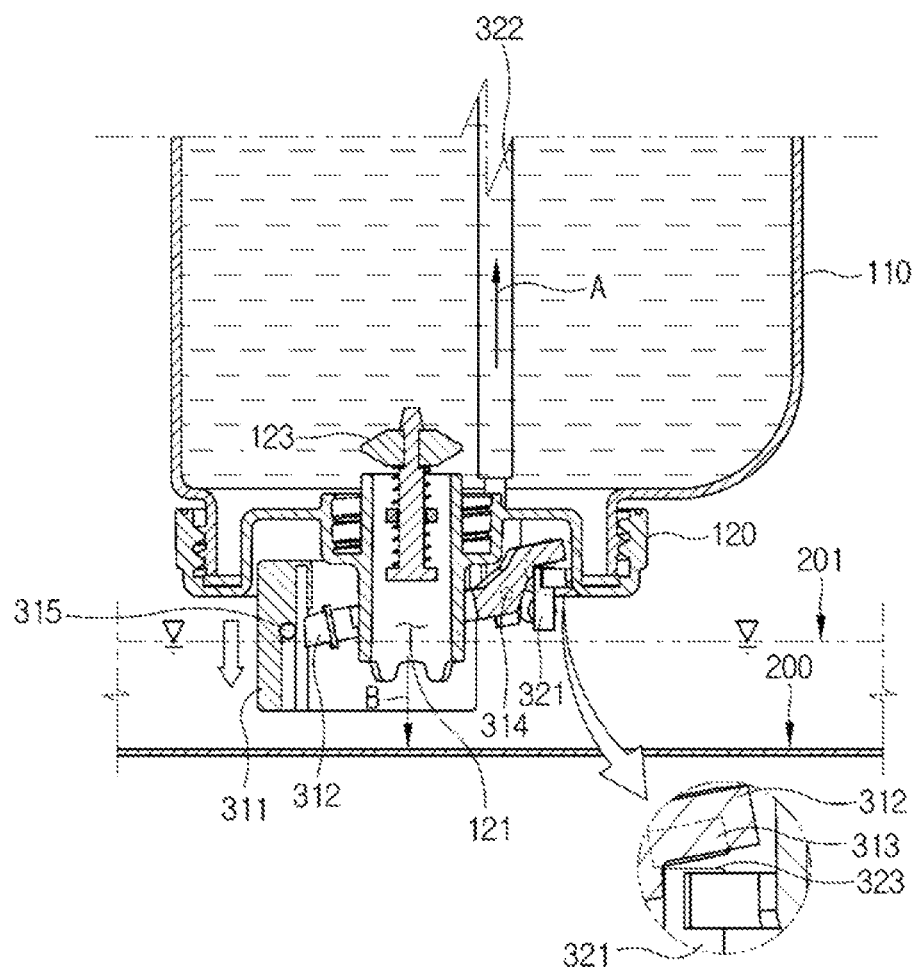
FIGS. 17A and 17B illustrate a process of water supply from the water tank of FIG. 12 to a water reservoir according to various embodiments of the present disclosure.
Figure 17B:
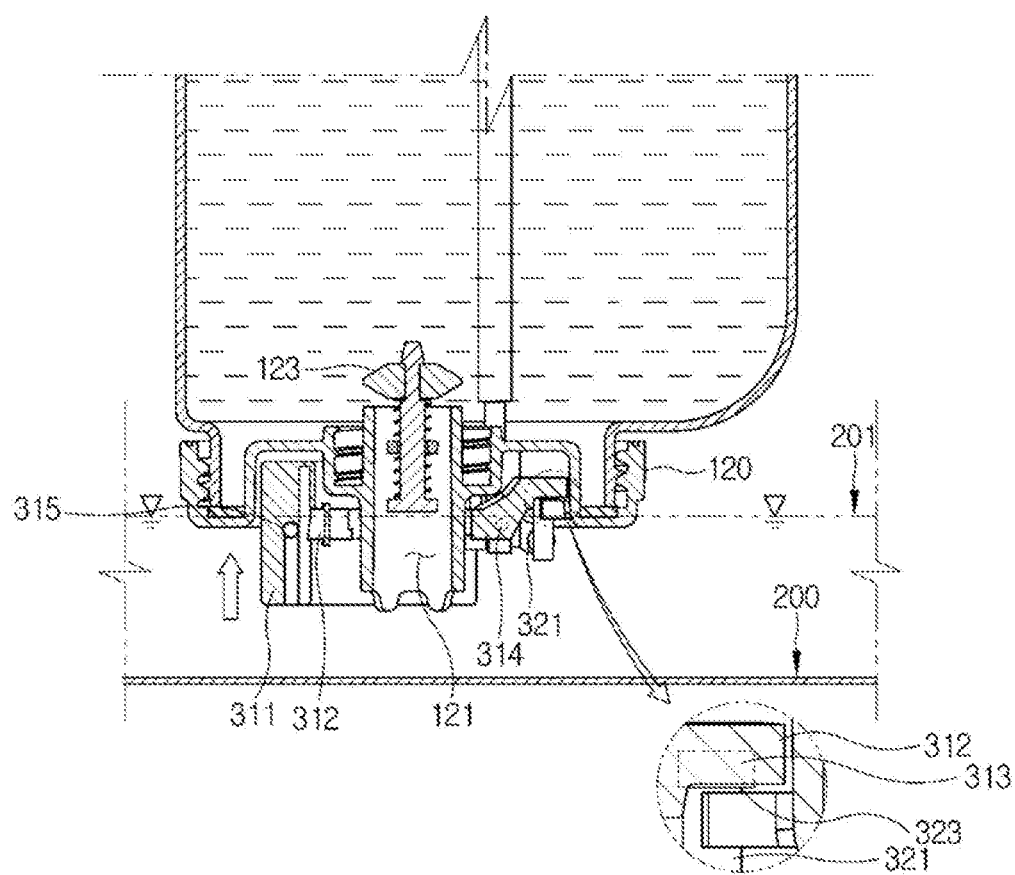

FIG. 12 is a front perspective view of a water tank, according to another embodiment of the present disclosure, and FIG. 13 is a perspective view of a bottom part of the water tank of FIG. 12, from which a cap is pulled apart. FIG. 14 is a bottom perspective view of a cap of the water tank of FIG. 12, FIG. 15 is an exploded view of a cap of the water tank of FIG. 12, and FIG. 16 is an exploded view of an open/close unit of the water tank of FIG. 12. FIGS. 17A and 17B illustrate a process of water supply from the water tank of FIG. 12 to a water reservoir.

Referring to FIG. 12, the air inflow device 300 is not installed in the body of the water tank 100, but in the cap 120 of the water tank 100. Accordingly, unlike the water tank shown in FIG. 4, no housing is formed in the body 110 of the water tank 100 to house the open/close unit 310.

Referring to FIGS. 13 to 16, the cap 120 of the water tank 100 of FIG. 14 has the same basic structure as that of the cap of the water tank of FIG. 4. The cap 120 may include the cap airtight member 122 for airtightly close the water tank 100 while the cap 120 is combined with the body 110. The cap airtight member 122 may be formed of an elastic material, such as rubber.

The cap 120 may also include the water supply inlet 121 for supplying water stored in the water tank 100 to the water reservoir 200. In the water supply inlet 121, the water supply valve 123 may be arranged to open the water supply inlet 121 while the water tank 100 is mounted in the humidifier 1, and to close the water supply inlet 121 while the water tank 100 is separated from the humidifier 1. The water supply valve 123 may be installed in the water supply inlet 121 by means of the elastic member 124. At this time, when the water tank 100 is mounted in the water reservoir 200 of the humidifier 1, the water supply valve 123 may be pushed up by a projection (not shown) formed in the water reservoir 200, to open the water supply inlet 121.

The air inflow device 300 installed in the cap 120 may include the air inflow path 320, and the open/close unit 310 to open or close the air inflow path 320. The open/close unit 310 may include the float 311 that is moved by buoyant force according to the water level 201 of the water reservoir 200, and the open/close member 312 for opening or closing the air inflow path 320 according to a height of the float 311. The open/close member 312 and the float 311 may be hinged through the hinge connector 315. The hinge connector 315 may combine the open/close member 312 and the float 311 by combining a hinge projection 315a formed on the open/close member 312 and a hinge projection receptor hole 315b formed on the float 311.

The float 311 may be formed in the form of a recess with the bottom face opened to float in water, or as shown in FIGS. 12 to 17, in the form of a box with the inside empty and closed.

The open/close member 312 has one end connected to the float 311 through the hinge connector 315, and the other end to open or close the air inflow path 320. The ends of the open/close member 312 moves like a seesaw, in order for the open/close member 312 to open the air inflow path 320 if the float 311 falls, and to close the air inflow path 320 if the float 311 rises.

The open/close member 312 may have the hinge projection 314 formed between both ends of the open/close member 312 to enable the ends to move like a seesaw. The hinge projection 314 of the open/close member 312 may be combined into the hinge projection receptor hole 112 formed in the cap 120.

The air inflow path 320 may include the air inflow pipe 321 formed in the cap 120 of the water tank 100, and the air tube 322 having one end connected to the air inflow pipe 321 to move the air upward of the inside of the water tank 100. The air flow inlet 323, which is opened or closed by the open/close unit 310, is formed on one end of the air inflow pipe 321, and the connection projection 324 to be connected to the air tube 322 is formed on the other end of the air inflow pipe 321. Specifically, the air flow inlet 323 is formed outside the water tank 100 if the cap 120 is mounted in the body 110, to be opened or closed by the open/close member 312, and the air tube connector projection 324 is arranged inside the water tank 100.

The air tube 322 is formed of a rubber or plastic material to couple with the connector projection 324 by fitting the connector projection 324 into the air tube 322. The air tube 322 may be formed of a non-flexible material to be able to deliver air from an end where the cap 120 is placed to the other end, or may be formed of a flexible material with sufficient length.

Although not shown, on an end of the air tube 322 not coupled with the connector projection 324, the check valve 400 may be arranged to prevent the water contained in the water tank 100 from flowing into the air tube 322.

The open/close unit 310 may include the airtight member 313 formed to airtightly close the air flow path 320, specifically, the air flow inlet 323 of the air inflow pipe 321. The airtight member 313 may be formed of a material such as rubber.

Referring to FIG. 17A and FIG. 17B, the float 311 of the open/close unit 310 may be moved up and down according to the height of the surface 201 of water of the water reservoir 200. As the float 311 moves up and down, the end of the open/close member 312 coupled with the float 311 at the hinge connector 315 may also be moved up and down. The hinge projection 314 placed between the one end and the other end of the open/close member 312 may be mounted into the hinge projection receptor hole 112 formed in the cap 120.

As one end of the open/close member 312 is moved up and down by the hinge connection between the open/close member 312 and the cap 120, the other end of the open/close member 312 may also be moved up and down accordingly. This rotation movement (seesaw movement) of the open/close member 312 may enable the other end of the open/close member 312 to open or close the air flow inlet 323 of the air inflow pipe 321.

The airtight member 313 may be arranged on the other end of the open/close member 312, i.e., the end to open or close the air flow inlet 323 to airtightly close the air flow inlet 323.

While the water tank 100 is mounted in the water reservoir 200, the air flow inlet 323 is arranged at a location farther away from the water reservoir 200 than from the water supply inlet 121 of the water tank 121. In other words, while the water tank 100 is mounted in the water reservoir 200, the air flow inlet 323 is located higher than the water supply inlet 121 of the water tank 121.

Because the highest water level 201 of the water reservoir 200 is below the air flow inlet 323, the water of the water reservoir 200 may not flow into the air flow inlet 323. Alternatively, even if the highest water level 201 of the water reservoir 200 is above the air flow inlet 323, the water of the water reservoir 200 may not flow into the air flow inlet 323 because the open/close member 312 airtightly closes the air flow inlet 323.

Referring to FIG. 17A, as the water contained in the water reservoir 200 is used by the humidifying element 70 for humidification, the water level 201 of the water reservoir 200 falls. As the water level 201 of the water reservoir 201 falls, the float 311 may fall. As the float 311 falls, the open/close member 312 turns around the hinge projection 314 to open the air flow inlet 323.

Even if the highest water level 201 of the water reservoir is above the air flow inlet 323, the water of the water reservoir 200 may not flow into the air inflow pipe 321 even when the air flow inlet 323 is opened by the open/close member 312 because the air flow inlet 323 is first exposed to air when the water level 201 falls.

When the open/close member 312 opens the air flow inlet 323, outside air flows into the air inflow pipe 321, and the air flowing in (A) may be moved upward of the inside of the water tank 100 along the air tube 322. Due to the air inflow (A), the water stored in the water tank 100 may be supplied (B) to the water reservoir 200 through the water supply inlet 121.

Referring to FIG. 17B, as the water level 201 rises due to the water supply (B), the float 311 rises, causing the open/close member 312 to turn again around the hinge projection 314 to close the air flow inlet 323. When the air flow inlet 323 is closed by the open/close member 312, a vacuum is created in the water tank 100, and the water supply (B) may be stopped by pressure equalization.

By repeating the water supply process, the water tank 100 of the humidifier 1 in accordance with an embodiment of the present disclosure may maintain the water level 201 of the water reservoir 200 to a constant level while fundamentally preventing noise from being produced by air bubbles flowing into the water tank 100.

Figure 18:
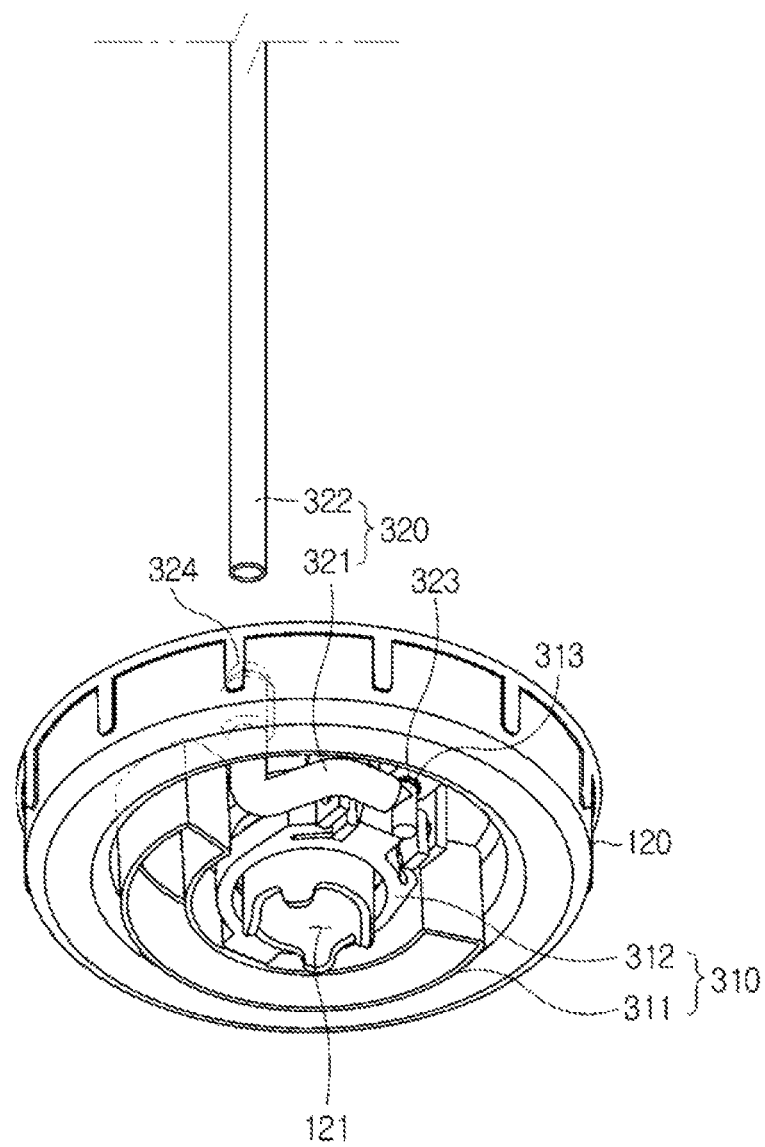
FIG. 18 illustrates a cap of a water tank according to various embodiments of the present disclosure.
Figure 19:
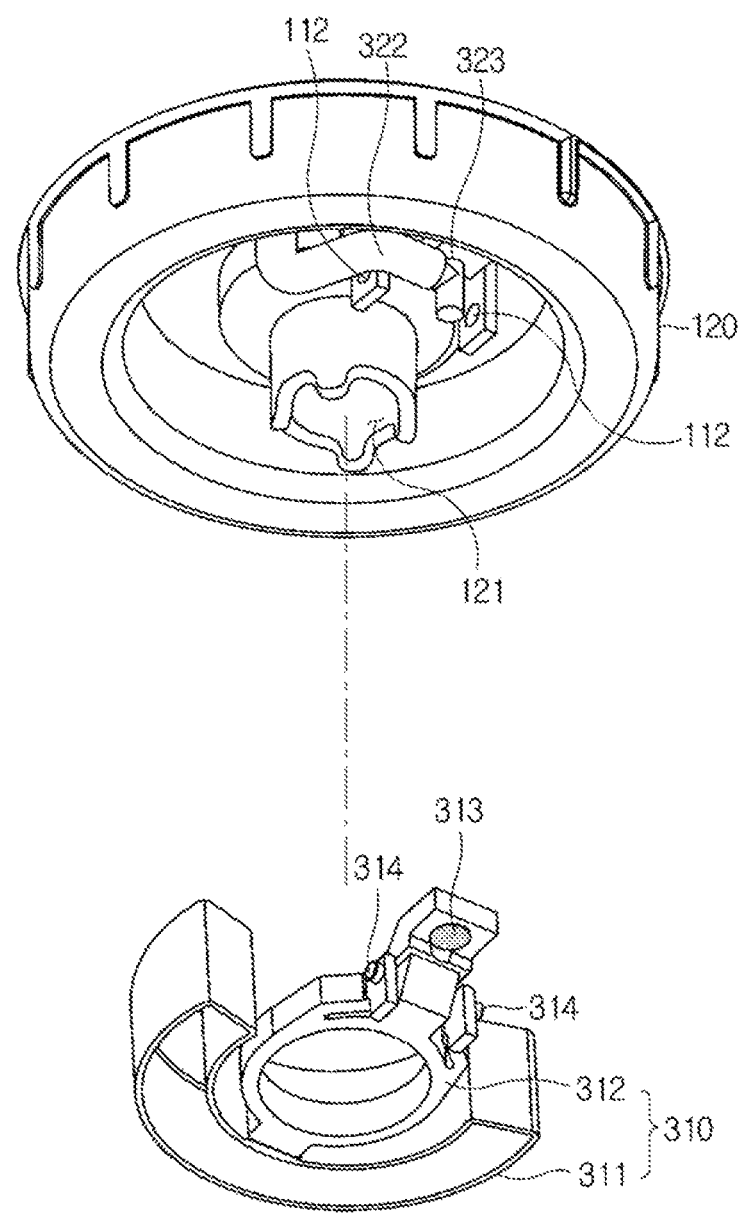
FIG. 19 illustrates a cap and an open/close unit of the water tank of FIG. 18, which are pulled apart according to various embodiments of the present disclosure.
Figure 20A:
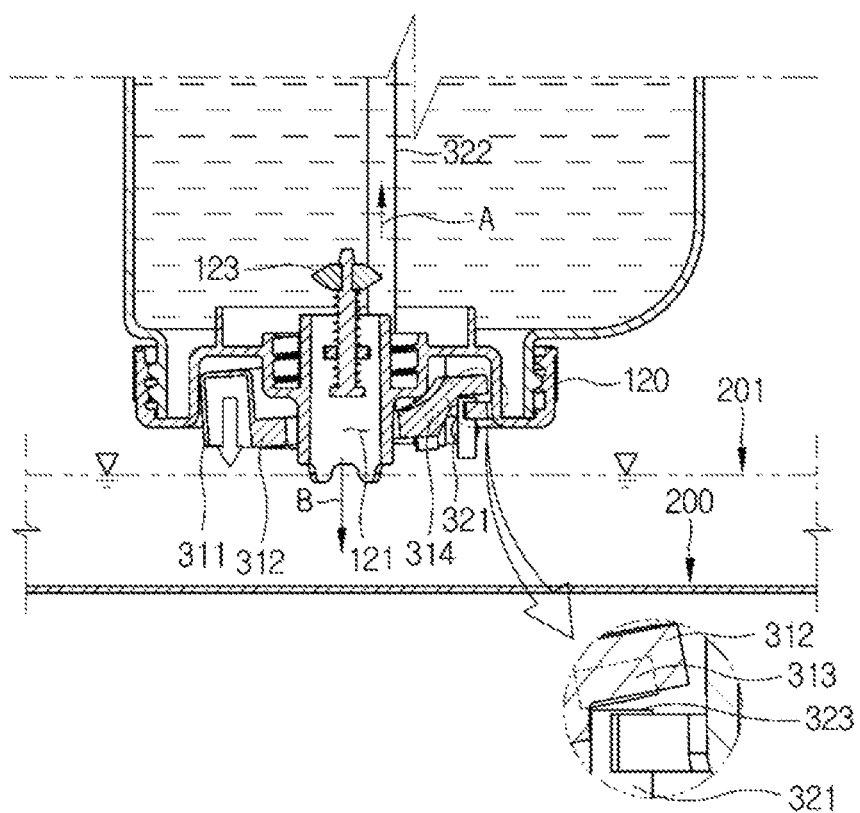
FIGS. 20A and 20B illustrate a process of water supply from the water tank of FIG. 18 to a water reservoir according to various embodiments of the present disclosure.
Figure 20B:
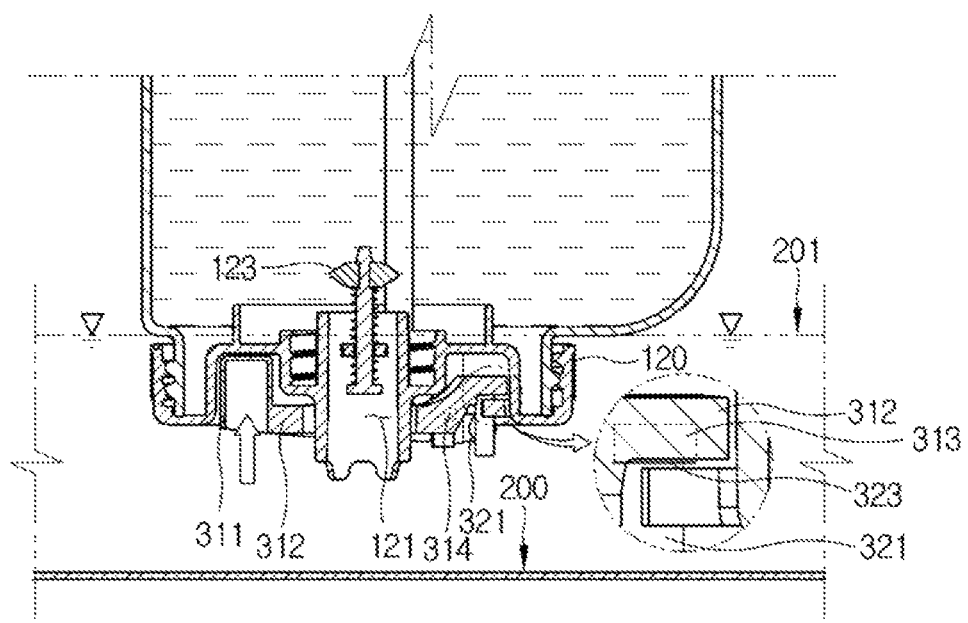

FIG. 18 is a bottom perspective view of a cap of a water tank, according to another embodiment of the present disclosure, and FIG. 19 is a perspective view of a cap and an open/close unit of the water tank of FIG. 18, which are pulled apart. FIGS. 20A and 20B illustrate a process of water supply from the water tank of FIG. 19 to a water reservoir.

A basic structure of the cap 120 of the water tank 100 of FIG. 18 is the same as that of the cap of the water tank of FIG. 12.

Description of the same parts of the structure will be omitted herein.

The float 311 may be formed with the inside empty or closed as shown in FIGS. 12 to 17 in order to float in water, or may be formed in the form of a recess with the bottom face opened as shown in FIGS. 18 to 20.

Unlike the open/close unit of the air inflow device installed in the cap of the water tank of FIG. 12, the open/close unit 310 of the air inflow device 300 installed in the cap 120 of the water tank 100 of FIG. 18 may be formed to have the float 311 and the open/close member 312 integrated in one unit. The integration of the open/close unit 310 and the float 311 in one unit may reduce the number of constituent parts and simplify the structure.

The open/close member 312 has one end integrally connected to the float 311, and the other end to be able to open or close the air inflow path 320. The ends of the open/close member 312 moves like a seesaw, in order for the open/close member 312 to open the air inflow path 320 if the float 311 falls, and to close the air inflow path 320 if the float 311 rises.

The open/close member 312 may have the hinge projection 314 formed between both ends of the open/close member 312 to enable the ends to move like a seesaw. The hinge projection 314 of the open/close member 312 may be combined into the hinge projection receptor hole 112 formed in the cap 120.

Referring to FIGS. 20A and 20B, the float 311 of the open/close unit 310 may be moved up and down according to the height of the surface 201 of water of the water reservoir 200. As the float 311 connected to one end of the open/close member 312 moves up and down, the other end of the open/close member 312 may be moved up and down. This rotation movement (seesaw movement) of the open/close member 312 may enable the other end of the open/close member 312 to open or close the air flow inlet 323 of the air inflow pipe 321.

Unlike the float of the open/close unit of the water tank shown in FIGS. 17A and 17B moving up and down at a level with the surface of water of the water reservoir, the float 311 of the open/close unit 310 of FIGS. 20A and 20B may turn around the hinge projection 314.

Figure 21:
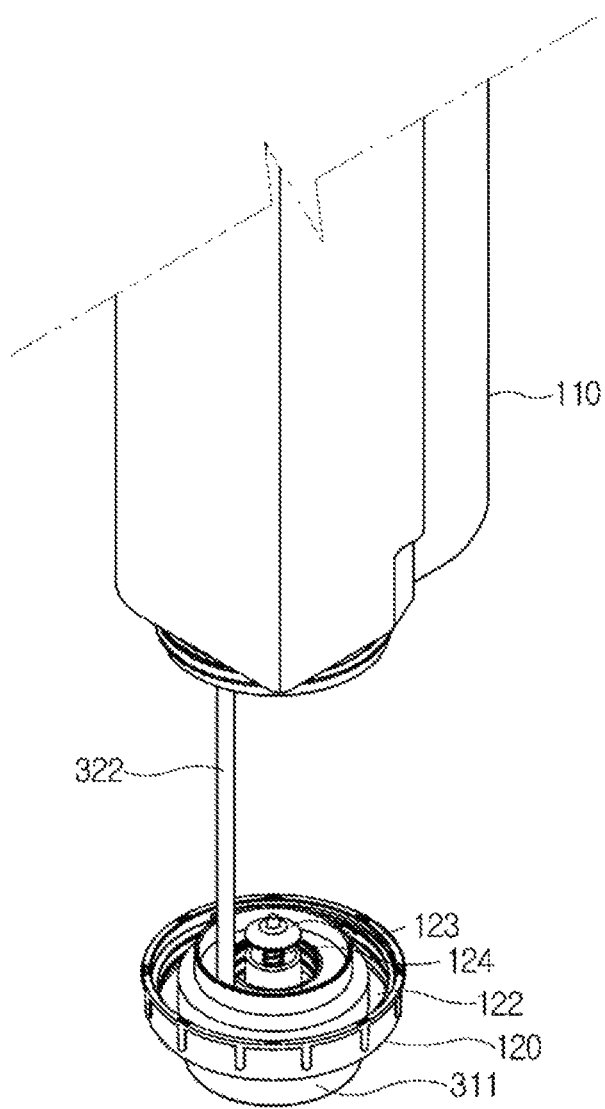
FIG. 21 illustrates a water tank with a cap pulled apart according to various embodiments of the present disclosure.
Figure 22:
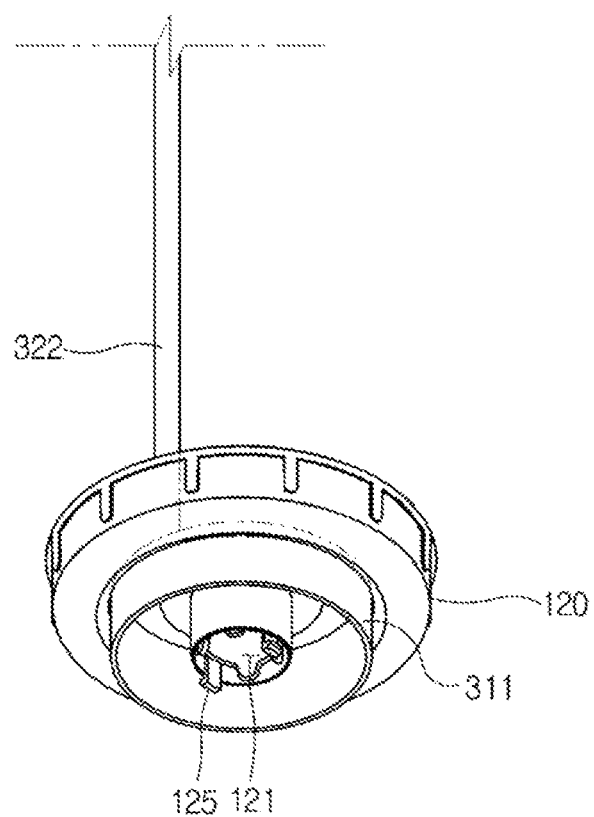
FIG. 22 is a bottom perspective view of a cap of the water tank of FIG. 21 according to various embodiments of the present disclosure.
Figure 23:
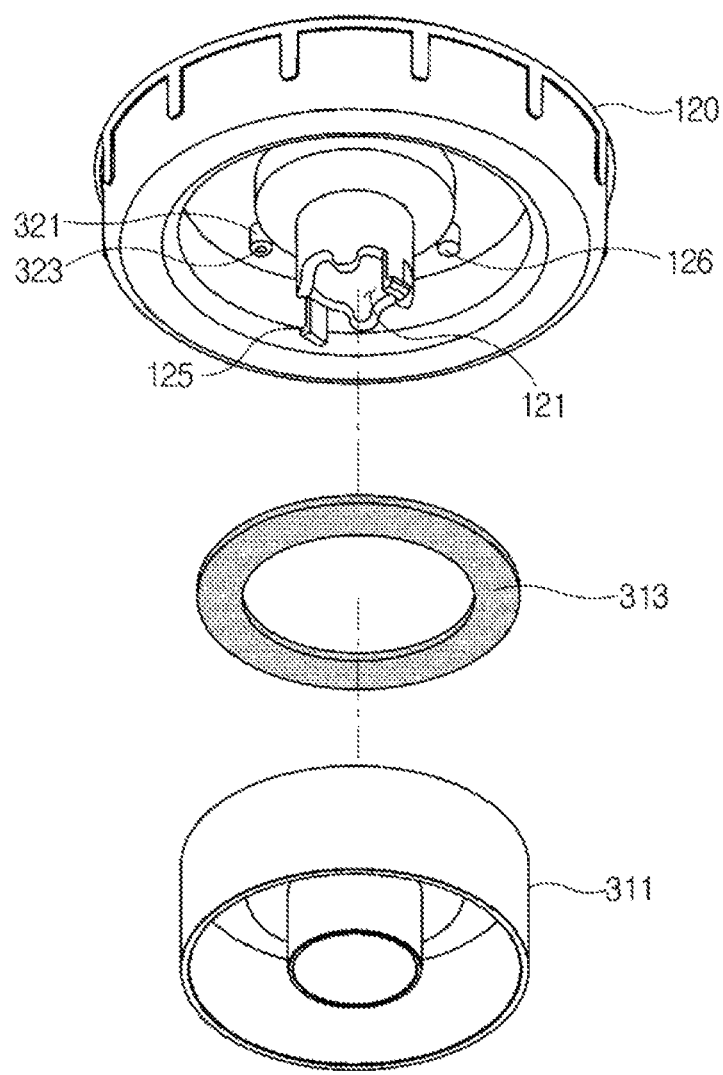
FIG. 23 illustrates a cap and an open/close unit of the water tank of FIG. 21, which are pulled apart according to various embodiments of the present disclosure.
Figure 24A:
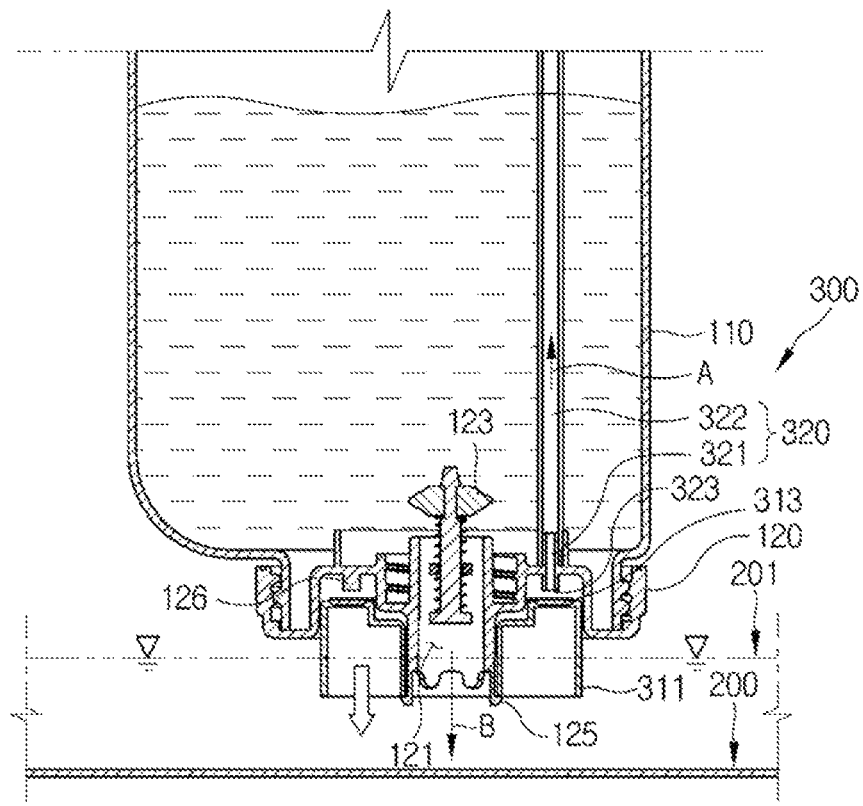
FIGS. 24A and 24B illustrate a process of water supply from the water tank of FIG. 21 to a water reservoir according to various embodiments of the present disclosure.
Figure 24B:
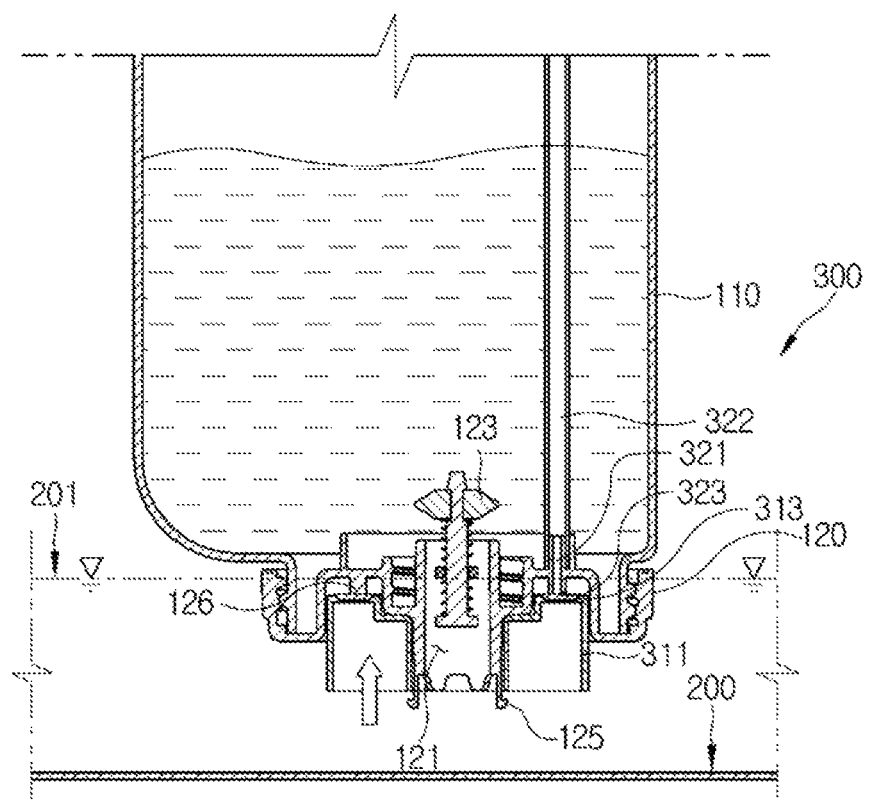

FIG. 21 is a perspective view of a water tank with a cap pulled apart, according to another embodiment of the present disclosure, FIG. 22 is a bottom perspective view of a cap of the water tank of FIG. 21, and FIG. 23 is a perspective view of a cap and an open/close unit of the water tank of FIG. 21, which are pulled apart. FIGS. 24A and 24B illustrate a process of water supply from the water tank of FIG. 21 to a water reservoir.

A basic structure of the cap 120 of the water tank 100 of FIG. 21 is the same as that of the cap of the water tank of FIG. 12. Description of the same parts of the structure will be omitted herein.

Referring to FIGS. 21 to 23, the air inflow device 300 installed in the cap 120 may include the air inflow path 320, and the float 311 to open or close the air inflow path 320. That is, the open/close unit may be configured only with the float 311.

The float 311 may be moved by buoyant force according to the water level 201 of the water reservoir 200, and the air inflow path 320 may be opened or closed according to the height of the float 311. The open/close member 312 may open the air inflow path 320 if the float 311 falls, and may close the air inflow path 320 if the float 311 rises.

The float 311 may be formed with the inside empty or closed in order to float in water, or may be formed in the form of a recess with the bottom face opened as shown in FIGS. 21 to 24.

The cap 120 may include an anti-separation structure 125 to prevent accidental separation of the float 311. The float 311 may have the form similar to a tire, which encloses the water supply inlet 121, and may be mounted in the cap 120 to enclose the water supply inlet 121. The anti-separation structure 125 may be formed at the end of the water supply inlet 121.

The air inflow path 320 may include the air inflow pipe 321 formed in the cap 120 of the water tank 100, and the air tube 322 having one end connected to the air inflow pipe 321 to move the air upward of the inside of the water tank. The air flow inlet 323, which is opened or closed by the float 311, is formed on one end of the air inflow pipe 321, and the connector projection 324 to be connected to the air tube 322 is formed on the other end of the air inflow pipe 321. Specifically, the air flow inlet 323 is formed outside the water tank 100 if the cap 120 is mounted in the body 110, to be opened or closed by the open/close member 311, and the air tube connector projection 324 is arranged inside the water tank 100.

The float 311 may include the airtight member 313 formed to airtightly close the air flow path 320, specifically, the air flow inlet 323 of the air inflow pipe 321. The airtight member 313 may be formed of a material such as rubber.

The cap 120 may include a supporting protrusion 126 formed to facilitate the float 311 to open or close the air flow inlet 323 by remaining level when the float 311 rises.

Referring to FIGS. 24A and 24B, the float 311 may be moved up and down according to the height of the surface 201 of water of the water reservoir 200. If the water level 201 of the water reservoir 200 increases, the float 311 may rise until the air flow inlet 323 and the supporting protrusion 126 come into contact with each other, to close the air flow inlet 323. If the water level 201 of the water reservoir 200 decreases, the float 311 falls until coming into contact with the anti-separation structure 125, to open the air flow inlet 323.

A home appliance equipped with the humidifier or water tank in accordance with the embodiments of the present disclosure may maintain a silent state of operation in an environment requiring low noise, and automatically control the water level by means of buoyant force without use of an electric valve unit, thereby reducing the manufacturing costs and achieving structural improvement.

In the meantime, even if the open/close unit may not be able to close the air inflow path due to a malfunction of the air inflow device of the home appliance equipped with the humidifier or water tank in accordance with the embodiments of the present disclosure, when the air flow inlet of the air inflow path is closed as the water level of the water reservoir increases, air inflow is blocked and water supply is stopped, thereby enabling normal water supply without overflowing of water from the water reservoir.

According to embodiments of the present disclosure, an air inflow path introduced separately from a water supply inlet in a water tank of a humidifier prevents noise generation due to air bubbles while water is supplied to a water reservoir from the water tank.

Furthermore, the air inflow path may be blocked to prevent water from flowing into the air inflow path during replenishment of water to the water tank of the humidifier.

Although the present disclosure has been described with an exemplary embodiment, various changes and modifications may be suggested to one skilled in the art. It is intended that the present disclosure encompass such changes and modifications as fall within the scope of the appended claims.

What is claimed is:

1. A humidifier comprising:
a water reservoir;
a water tank configured to store water, the water tank including a water supply valve configured to open a water supply inlet to supply the water to the water reservoir while the water tank is coupled to the water reservoir and to close the water supply inlet while the water tank is separated from the water reservoir;
an air inflow portion through which air is supplied to the water tank, the air inflow portion is separate from the water supply inlet;
a float disposed between the water tank and the water reservoir in a vertical direction and configured to move up and down according to a water level of the water reservoir, wherein when the float moves down, the water is supplied to the water reservoir from the water tank through the water supply inlet;
a humidifying element rotatably supported by a support frame; and
a fan configured to produce an air current for evaporating water supplied from the water reservoir to the humidifying element,
wherein the water supply valve of the water tank is configured to be pushed up by a projection portion associated with the water reservoir to open the water supply inlet when the water tank is coupled to the water reservoir.

2. The humidifier of claim 1, wherein the float has a form of a tire to enclose the water supply inlet.

3. The humidifier of claim 1, wherein the water supply valve is installed in the water supply inlet by an elastic member.

4. The humidifier of claim 1, further comprising:
an airtight member coupled to the float to move together with the float.

5. The humidifier of claim 4, wherein the airtight member is formed of rubber material.

6. The humidifier of claim 1, wherein an amount of air supplied to the water tank and an amount of water flowing in the water reservoir correspond to each other.

7. The humidifier of claim 1, wherein the humidifying element is configured to perform humidification with supplied water contained in the water reservoir.

8. The humidifier of claim 1, further comprising:
a main frame constituting an exterior, wherein the fan is placed inside the main frame for circulating air.

9. The humidifier of claim 8, wherein an outlet is formed on a top of the main frame and the fan is disposed below the outlet.

10. The humidifier of claim 9, wherein the air circulated by the fan first passes through the humidifying element and then passes through the fan to the outlet.

11. The humidifier of claim 8, further comprising:
a filter unit configured to purify air flowing into the main frame and disposed in the main frame.

12. The humidifier of claim 11, wherein the filter unit is capable of being lifted upward and separated from the main frame.

13. The humidifier of claim 12, wherein an outlet is formed on a top of the main frame and the fan is disposed below the outlet, and
wherein the air circulated by the fan is transmitted to the outlet by sequentially passing through the filter unit, the humidifying element, and the fan.

14. The humidifier of claim 1, wherein the water supply inlet is provided at a bottom of the water tank.

15. The humidifier of claim 1, wherein the support frame is connected to the water reservoir.

16. The humidifier of claim 1, wherein the float is disposed in an open/close unit disposed on the water tank.

* * * * *